United States Patent
Phaneuf et al.

(10) Patent No.: US 10,441,550 B2
(45) Date of Patent: *Oct. 15, 2019

(54) NANOFIBROUS MATERIALS AS DRUG, PROTEIN, OR GENETIC RELEASE VEHICLES

(71) Applicants: BioSurfaces, Inc., Ashland, MA (US); Clemson University, Clemson, SC (US); Rhode Island Board of Education, Providence, RI (US)

(72) Inventors: Matthew D. Phaneuf, Ashland, MA (US); Philip J. Brown, Williamston, SC (US); Martin J. Bide, Hope Valley, RI (US)

(73) Assignees: BIOSURFACES, INC., Ashland, MA (US); RHODE ISLAND BOARD OF EDUCATION, Providence, RI (US); CLEMSON UNIVERSITY, Clemson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/046,675

(22) Filed: Feb. 18, 2016

(65) Prior Publication Data

US 2016/0158160 A1 Jun. 9, 2016

Related U.S. Application Data

(63) Continuation of application No. 14/293,481, filed on Jun. 2, 2014, which is a continuation-in-part of application No. 13/303,319, filed on Nov. 23, 2011, now Pat. No. 8,771,582, which is a continuation-in-part of application No. 12/954,829, filed on Nov. 26, 2010, now Pat. No. 8,691,543, and a continuation-in-part of application No. 11/366,165, filed on Mar. 2, 2006, now abandoned, which is a continuation-in-part of application No. 11/211,935, filed on Aug. 25, 2005, now Pat. No. 7,413,575.

(60) Provisional application No. 61/264,440, filed on Nov. 25, 2009, provisional application No. 60/658,438, filed on Mar. 4, 2005.

(51) Int. Cl.

| A61K 9/70 | (2006.01) |
| A61K 31/4196 | (2006.01) |
| A61K 31/337 | (2006.01) |
| A61K 31/496 | (2006.01) |
| A61K 9/00 | (2006.01) |
| D04H 1/435 | (2012.01) |
| D04H 1/728 | (2012.01) |
| D04H 3/011 | (2012.01) |
| D04H 3/02 | (2006.01) |
| D04H 3/16 | (2006.01) |
| D01D 1/02 | (2006.01) |
| D01D 5/00 | (2006.01) |
| D01F 6/62 | (2006.01) |
| B29C 48/05 | (2019.01) |
| A61F 2/82 | (2013.01) |
| B29C 48/00 | (2019.01) |

(52) U.S. Cl.
CPC ......... *A61K 9/7007* (2013.01); *A61K 9/0092* (2013.01); *A61K 31/337* (2013.01); *A61K 31/4196* (2013.01); *A61K 31/496* (2013.01); *B29C 48/05* (2019.02); *D01D 1/02* (2013.01); *D01D 5/0038* (2013.01); *D01F 6/62* (2013.01); *D04H 1/435* (2013.01); *D04H 1/728* (2013.01); *D04H 3/011* (2013.01); *D04H 3/02* (2013.01); *D04H 3/16* (2013.01); *A61F 2/82* (2013.01); *A61K 9/70* (2013.01); *B29C 48/022* (2019.02)

(58) Field of Classification Search
CPC ........... A61F 2/82; A61K 9/0092; A61K 9/70; A61K 9/7007; D01D 1/02; D01D 5/0038; D04H 1/728
See application file for complete search history.

(56) References Cited

U.S. PATENT DOCUMENTS

| 4,464,295 A | 8/1984 | Bhaduri et al. |
| 6,308,509 B1 * | 10/2001 | Scardino .................. A61F 2/28 57/402 |
| 6,518,033 B1 | 2/2003 | Gromeier et al. |
| (Continued) | | |

FOREIGN PATENT DOCUMENTS

| CN | 101439200 A | | 5/2009 |
| WO | WO2002074190 | * | 9/2002 |
| WO | WO2012-097229 A2 | | 7/2012 |

OTHER PUBLICATIONS

Recum et al. (Electrospinning: Applications in drug delivery and tissue engineering, Biomaterials, 2008, pp. 1989-2006).*

(Continued)

*Primary Examiner* — Anna R Falkowitz
(74) *Attorney, Agent, or Firm* — Barclay Damon, LLP

(57) ABSTRACT

The present invention is a bioactive, nanofibrous material construct which is manufactured using a unique electrospinning perfusion methodology. One embodiment provides a nanofibrous biocomposite material formed as a discrete textile fabric from a prepared liquid admixture of (i) a non-biodegradable durable synthetic polymer; (ii) a biologically active agent; and (iii) a liquid organic carrier. These biologically-active agents are chemical compounds which retain their recognized biological activity both before and after becoming non-permanently bound to the formed textile material; and will become subsequently released in-situ as discrete freely mobile agents front the fabric upon uptake of water from the ambient environment.

22 Claims, 6 Drawing Sheets

(56) References Cited

U.S. PATENT DOCUMENTS

| | | | |
|---|---|---|---|
| 6,689,166 | B2 | 2/2004 | Laurencin et al. |
| 6,713,011 | B2 | 3/2004 | Chu et al. |
| 7,255,741 | B2 | 8/2007 | Goud et al. |
| 7,374,774 | B2 | 5/2008 | Bowlin et al. |
| 7,413,575 | B2 | 8/2008 | Phaneuf et al. |
| 7,776,574 | B2 | 8/2010 | Mahadevan et al. |
| 8,158,806 | B2 | 4/2012 | Sengupta et al. |
| 8,170,665 | B2 | 5/2012 | Cohen et al. |
| 8,236,296 | B2 | 8/2012 | Rosen et al. |
| 8,771,582 | B2 * | 7/2014 | Phaneuf ............... A61K 9/0092 264/210.1 |
| 2002/0084178 | A1 | 7/2002 | Dubson ............... A61F 2/06 204/157.6 |
| 2003/0195611 | A1 | 10/2003 | Greenhalgh et al. |
| 2003/0211135 | A1 * | 11/2003 | Greenhalgh ............... A61F 2/07 424/443 |
| 2004/0054406 | A1 * | 3/2004 | Dubson ............... A61F 2/06 623/1.39 |
| 2004/0086544 | A1 | 5/2004 | Bezemer et al. |
| 2004/0199241 | A1 | 10/2004 | Gravett et al. |
| 2005/0095695 | A1 | 5/2005 | Shindler et al. |
| 2005/0158362 | A1 | 7/2005 | Wheatley et al. |
| 2005/0283218 | A1 | 12/2005 | Williams |
| 2006/0200232 | A1 | 9/2006 | Phaneuf et al. |
| 2007/0112115 | A1 | 5/2007 | Shalaby et al. |
| 2008/0009830 | A1 | 1/2008 | Fujimoto et al. |
| 2009/0142505 | A1 * | 6/2009 | Orr ............... B05B 5/08 427/458 |
| 2009/0192609 | A1 | 7/2009 | Klabunde et al. |
| 2010/0129450 | A1 | 5/2010 | Atala et al. |
| 2010/0129656 | A1 | 5/2010 | Zussman et al. |
| 2010/0166854 | A1 | 7/2010 | Michniak-Kohn et al. |
| 2011/0142804 | A1 * | 6/2011 | Gaudette ............... A61L 27/18 424/93.7 |
| 2011/0270411 | A1 | 11/2011 | Yang et al. |
| 2012/0068384 | A1 | 3/2012 | Phaneuf |
| 2014/0054828 | A9 | 2/2014 | Phaneuf et al. |
| 2014/0271795 | A1 * | 9/2014 | Phaneuf ............... A61K 31/496 424/443 |
| 2016/0158160 | A1 | 6/2016 | Phaneuf et al. |

OTHER PUBLICATIONS

Han et al. (Fabrication of drug-loaded electrospun aligned fibrous threads for suture applications, J. Biomed. Materials Res. Part A, 2008, pp. 80-95).*

WIPO, International Preliminary Report on Patentability (IPRP) from PCT Appl. No. PCT/US2015/033532, dated Dec. 6, 2016 (total 7 pages).

Bernard, Stephen A. et al., Resuscitation Journal—Official Journal of the European Resuscitation Council, "Therapeutic hypothermia induced during cardiopulmonary resuscitation using large-volume, ice cold intravenous fluid", (DOI:DOI: http://dx.doi.org/10.1016/i.) found at http://www.resuscitationjournal.com/article/S0300-9572(07)00386-3/fulltext, published Feb. 2008, vol. 76, Issue 2, pp. 311-313, total 2 pages).

Britton, D. et al.., Acta Crystallographica Section E, Crystallographic Communications, "Two new polytypes of 2,4,6-tribromobenzonitrile", published online Jan. 13, 2016 (DOI: 10.1107/S2056969016000256), found at http://www.ncbi.nlm.nih.gov/pmc/articles/PMC4770976/ (total 10 pages).

Richardson, Ben D. et al., PLOS, a Peer-Reviewed, Open Access Journal, "Extrasynaptic $GAB_A$ Receptors and Tonic Inhibition in Rat Auditory Thalamus", published online Jan. 26, 2011 (DOI: 10.1371/journal.pone.0016508) found at http://www.ncbi.nlm.nih.gov/pmc/articles/PMC3027696/ (total 8 pages).

Wang, Ken et al., American Journal of Physiology, Heart and Circulatory Physiology, American Physiology Society, published online Jan. 16, 2015 (DOI: 10.1152/aipheart.00556.2014) found at http://www.ncbi.nlm.nih.gov/pmc/articles/PMC4551126/ (total 19 pages).

European Patent Office, International Search Report from PCT/US2015/033532 dated Sep. 4, 2015.

Koenig et al. in A review of polymer dissolution, Prog. Polym. Sci., 2003, p. 1223-1270.

U. S. Patent and Trademark Office (ISA/US), International Search Report and Written Opinion from PCT Application Nol. PCT/US2017/018383 as completed Apr. 28, 2017.

* cited by examiner

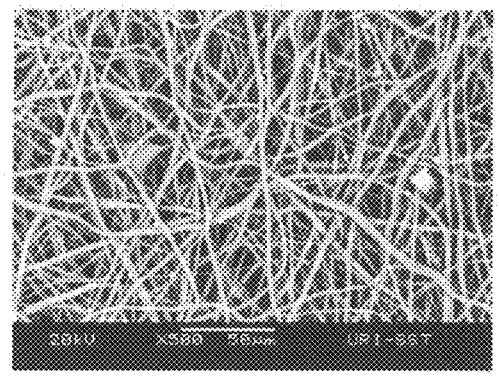 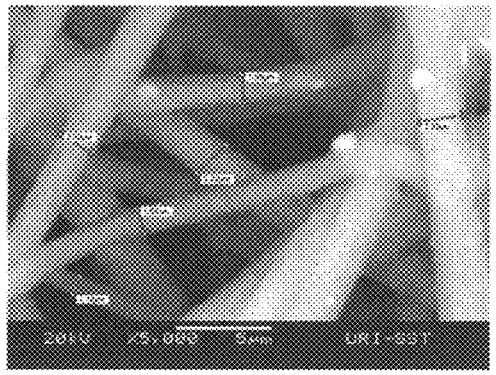
FIG. 5A   FIG. 5B
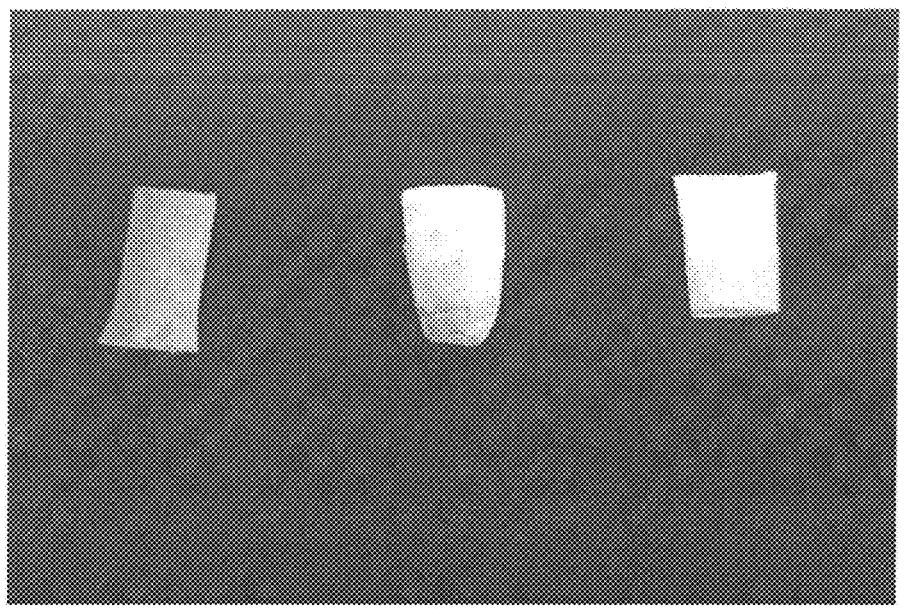
FIG. 6

NANOFIBROUS MATERIALS AS DRUG, PROTEIN, OR GENETIC RELEASE VEHICLES

CROSS-REFERENCE TO RELATED APPLICATIONS

This application is a continuation of U.S. Ser. No. 14/293,481 (filed Jun. 2, 2014), which is; a continuation-in-part of U.S. Ser. No. 13/303,319, filed Nov. 23, 2011 (now issued U.S. Pat. No. 8,771,582), which is a continuation-in-part of U.S. Ser. No. 12/954,829, filed Nov. 26, 2010 (now issued U.S. Pat. No. 8,691,543), which claims priority to U.S. Provisional Application 61/264,440, filed Nov. 25, 2009. The aforementioned U.S. Ser. No. 13/303,319 is also a continuation-in-part of U.S. Ser. No. 11/366,165, filed Mar. 2, 2006 (abandoned) which is a continuation-in-part of U.S. Ser. No. 11/211,935, filed Aug. 25, 2005 (now issued U.S. Pat. No. 7,413,575), which claims priority to U.S. Provisional Application 60/658,438 (filed Mar. 4, 2005). The above-identified patent applications are hereby incorporated by reference in their entirety.

FIELD OF THE INVENTION

The instant invention provides a variety of non-biodegradable, formed fabric materials, articles, and devices suitable for the in-situ delivery of many different biologically-active agents. The disclosure also offers a wide range of fabricated nanofibrous textiles having varying and diverse individual biologic properties, or combinations thereof; and provides medical products which are resistant to breakage and tearing as well as demonstrate a specifically desired localized effect such as resistance to infection-properties which will aid in reducing both the morbidity and mortality of a person afflicted with an injury or ailment.

BACKGROUND

There are over 13 million medical articles and devices utilized annually in the United States for prophylactic and/or therapeutic treatment. These items range in sophistication from simple devices such as hernia repair mesh, wound dressings and catheter cuffs—to more complex implantable devices such as the total implantable heart, left ventricular assist devices and prosthetic arterial grafts. Although utilization of these medical articles and devices has improved the health and quality of life for the patient population as a whole, the in-vivo application of all such medical implements are prone to two major kinds of complications: injection and incomplete/non-specific cellular healing.

In general, regardless of the particular causative agent, infection remains one of the major complications associated with utilizing biomaterials, with the clinical infection occurring at either acute or delayed time periods after in-vivo use or implantation of the medical article or device. Today, surgical site infections account for approximately 14-16% of the 2.4-million nosocomial infections in the United States, and result in an increased patient morbidity and mortality. The inherent bulk properties of various biomaterials that comprise these articles and devices typically provide a milieu for initial bacterial/fungus adhesion with subsequent biofilm production and growth.

Similarly, unregulated cellular growth affects various medical devices such as stents and vascular grafts. Occlusion rates for diseased blood vessels after placement of a bare metallic stent (restenosis) have been reported as high as 27%, a significant problem based on the 1.1 million stents annually implanted. Moreover, since the currently available biomaterials in these medical articles and devices are typically comprised of foreign polymeric compounds, these biomaterials do not emulate the multitude of dynamic biologic and healing processes that occur in normal tissue; and consequently, the cellular components normally present within native living tissue are not available for controlling and/or regulating the reparative process. Thus, the search continues today for novel biomaterials (such as drug releasing biomaterials) that would direct or enhance some of the normal healing processes of native tissue, and would decrease patient morbidity and mortality rates.

Currently, drug delivery from a majority of implantable medical devices such as stents is achieved via the coating/sealing of a device or scaffold with a biodegradable polymer composition which serves as a drug reservoir. There are several potential problems with utilizing this system in that: (1) polymer coating onto the device can be inconsistent, resulting in areas with minimum/no localized drug release; (2) polymer coating efficiency can be limited based on the device design or composition of the base material; (3) drug release is dependent on biodegradation of the polymer reservoir, resulting in inconsistent drug release; and (4) application of the exogenous polymer can have adverse effects on tissue/organ healing or upon the biocompatibility (i.e. increasing thrombogenecity) of the original implant.

Electrospinning provides a technique for making nanofibrous material substrates. Electrospinning to produce nanoscale fibers, fabrications and textiles, however, is still a manufacturing technique in need of further development and refinement. Utilization of electrospinning as a technique to synthesize various nanofibrous materials from polymers such as polyurethane, polyvinyl alcohol (or "PVA"), poly (lactic glycolic) acid (or "PLGA"), nylon, and polyethylene oxide has been investigated for several decades (see for example Subbiah et al., "Electrospinning Of Nanofibers", J. Applied Polymer Sci. 96:557-569 (2005).

While inclusion of bioactive agents has been accomplished for several other polymers (such as polyurethane, PLGA, alginate and collagen), the electrospinning technique has not been realized for polyethylene terephthalate ("PET"), or "polyester" as understood generally in textile circles, until recently. Since then. Ma et al. was able to electrospin polyethylene terephthalate using a melt-spinning technology (see Ma Z, Kotaki M, Yong T, He W, Ramakrishna S., "Surface engineering of electrospun polyethylene terephthalate (PET) nanofibers towards development of a new material for blood vessel engineering", Biomaterials 26:2527 (2005)). However, the Ma et al. reported technique requires a surface modification in which formaldehyde and several cross-linkers were utilized post-spinning subsequently to incorporate gelatin, owing to the high temperatures employed in their manufacturing process. These modification procedures are and remain a major issue because of their high temperature requirements and the consequential failure of the protein (or other temperature sensitive agent) to maintain its characteristic biological activity throughout the material fabrication process.

Accordingly, despite all these developments to date, there remains a recognized and continuing need for further improvements in the making of medical devices and articles comprised of nanofibrous materials which would demonstrate adequate physical strength characteristics and durability as fabricated items, and which would serve as biomedical constructs formed of fibrous materials having demonstrable biologically active properties. All such improvements in the making and/or preparation of such nanofibrous materials and articles would be readily seen as a major advantage and outstanding benefit in the medical field.

SUMMARY OF THE INVENTION

The present invention is a major advance in the development of biomedical materials, devices and constructs. Accordingly, the invention has multiple aspects, some of which may be defined as follows.

A first aspect provides a method for forming a fabricated textile suitable for use as a medical article. The method includes the steps of dissolving a non-biodegradable polymer and a pre-chosen biologically-active agent in an organic solvent at an ice-cold temperature. Once dissolved, the admixture is permitted to warm before electrospinning at room temperature to form the fabricated textile.

BRIEF DESCRIPTION OF THE DRAWINGS

The present invention is disclosed with reference to the accompanying drawings, wherein:

The present invention may be more easily understood and more readily appreciated when taken into conjunction with the accompanying drawing, in which:

FIG. 5A and FIG. 5B are scanning electron microphotographs of a nPET (electrospun polyethylene terephthalate) textile segment showing the diameter size of the fibers within the nanofibrous material;

FIG. 6 is an overhead view of the UV illumination differences between nPET segments, nPET-Cipro segments, and nPET-Diflucan segments;

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
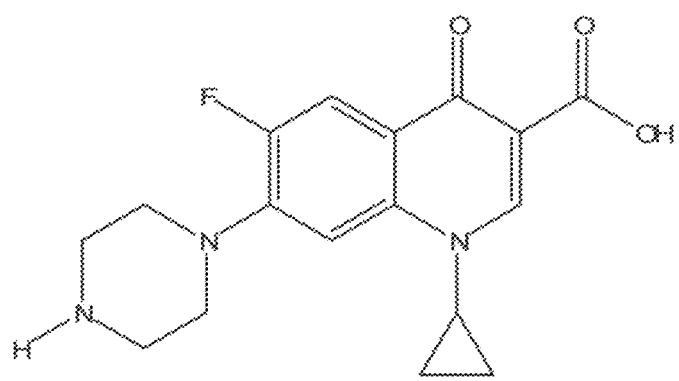
FIG. 1 is an illustration of the chemical structure of Ciprofloxacin.

Disclosed in this specification is a bioactive, nanofibrous material construct which is manufactured either in tubular or flat sheet form using an unique electrospinning perfusion methodology. One particular embodiment provides a nanofibrous biocomposite material formed as a discrete textile fabric from a prepared liquid admixture of (i) a biodurable synthetic polymer; (ii) a biologically active agent; and (iii) a liquid organic carrier. The prepared liquid admixture of diverse compositions is employed in a novel electrospinning perfusion process to form an agent-releasing textile comprised of nanofibrous material, which in turn, can serve as the antecedent precursor and tangible workpiece for subsequently making the desired medical article or device suitable for use in-vivo. Prior art medical devices generally includes an underlying non-polymeric support (e.g. scaffold, stent, etc) and coat the support with a biodegradable polymer and then soaks the resulting coated support in a biologically-active agent to embed the agent in the polymer. In contrast, the medical devices of the present invention are discrete articles that omit the underlying scaffold and the medical devices consist essentially of a non-biodegradable polymer that has the biologically-active agent embedded therein. The materials of the present invention have mechanical properties which are sufficient to permit the manufacturer to omit the scaffolds that were previously required by the prior art.

After the agent-releasing textile has been fabricated as a discrete article, one or more pre-chosen biologically-active agents will have become non-permanently immobilized and releasably bound to the tangible nanofibrous material of the fabricated textile. These non-permanently immobilized biologically-active agents are well established chemical compounds which retain their recognized biological activity both before and after becoming impermanently (i.e., temporarily or reversibly) bound to the textile fabric; and will become subsequently released in-situ and directly delivered into the ambient environment as discrete mobile entities when the textile fabric lakes up any fluid—i.e., any aqueous or organic based liquid. Accordingly, via the transitory immobilization of one or more biologically active molecules to the nanofibrous biocomposite material, the agent-releasing textile is very suitable for inclusion and use in-vivo as a clinical/therapeutic construct.

The present electrospinning perfusion method of making agent-releasing nanofibrous textiles provides several major advantages and desirable benefits to the commercial manufacturer as well as to the physician and surgeon. Among these are the following:

First, the manufacturing methodology comprising the present invention docs not utilize any immersion techniques and does not require submerging the fabricated textile in any immersion baths, soaking tanks, or dipping pools for any purpose. Rather, the methodology preferably utilizes the unique technique of electrospinning perfusion as a manufacturing method in order to blend a synthetic substance and a biologically active agent of choice together as a fabricated textile.

Second, the electrospinning perfusion method of manufacture yields a fabricated textile having particular characteristics. The fabricated textile is initially fashioned either as an elongated hollow tube having two discrete open tubular ends and fixed inner and outer wall diameters; or as a flat or planar sheet of nanofibrous fabric. In either format, the fabricated textile can be folded, or twisted, and otherwise manipulated to meet specific requirements of thickness, gauge, or deniers; and can also be cut, split, tailored, and conformed to meet particular shapes, configurations and patterns.

Third, the fabricated textile is a nanofibrous material composite comprised of multiple fibers, has a determinable individual fiber thickness in or near the nanometer size range (typically less than 2 microns), and presents a discernible fiber organization and distribution pattern. These fabricated textiles provide and demonstrate excellent suture retention, burst strength, break strength, tear strength and/or biodurability.

Fourth, the manufacturing method comprising the present invention employs limited heat and compression force to alter the exterior surface of the fabricated textile originally formed via the electrospinning perfusion technique. This exterior surface treatment portion of the manufacturing process is optional, but when employed, will produce a highly desirable crimped exterior surface over the entire linear length of the fabricated textile article. A notable feature of this exterior surface treatment procedure is that the inner diameter size (typically less than 1 mm to not greater than about 30 mm, but can vary from these particular parameters) of the fabricated textile remains constant and uniform, despite the effects of the limited heating and compression treatment of the textile exterior surface.

Fifth, the biologically active agent will retain its characteristic biological activity both before and after being temporarily bound to the nanofibrous material. The attributes and properties associated with the biologically active agent of choice will co-exist with and be an integrated feature of the resulting textile article at the time it is utilized.

The Agent-Releasing Nanofibrous Textile and its Role as an Antecedent in the Making of a Prepared Medical Article or Device The method of the present invention is directed in part to the making of an agent-releasing textile, an antecedent article of manufacture, which is then employed as a tangible workpiece to generate a subsequently prepared medical article or device suitable for use in-vivo. An agent-releasing textile is a fabricated textile comprising nanofibrous matter which has at least one biologically active agent immobilized onto and/or within the material substance of the textile; and which, upon wetting, is then able to release the biologically active agent in-situ and deliver it in a functionally operative form into the adjacent local area or immediately surrounding environment. Such a prepared nanofibrous textile must provide and release at least one active chemical composition, compound, or molecule which is active, functional and operative either to influence and/or to initiate or cause a recognizable pharmacological effect or determinable physiological change in the living cells, tissues and organs of the host patient. A fabricated textile is an article of manufacture which is comprised, in whole or in part, of fibers arranged as a fabric. The fibers comprising the fabricated textile may be chosen from a diverse range of organic synthetics, prepared polymer compounds, or naturally-occurring matter. In general, the fabricated textile is often prepared as a cloth or fabric; and may comprise a single fiber film, or a single layer of fibrous matter; or exist as multiple and different deniers of fibers which are present in a range of varying thickness, dimensions, and configurations.

It will be appreciated that, after the agent-releasing nanofibrous textile has been manufactured and is present as a discrete entity, it can optionally serve as a tangible workpiece in combination with other items and additional components and hardware to yield the desired end product, a clinically or therapeutically useful "medical article or device". Thus, regardless of its true chemical composition/formulation or the particular mode of construction, the initially formed "agent-releasing textile" and the subsequently generated "medical article or device" are directly and intimately related; and thus share a number of specific qualities and characteristics in common. These mutually shared attributes include:

(i) Each agent-releasing textile is formed as an elongated hollow tube having a determinable overall tubular length and two open ends; has at least one internal lumen of determinable volume which is co-incidental and coextensive with the internal wall surface; and has at least one exterior wall surface which is co-incidental and co-extensive with the outer wall topography.

(ii) Each agent-releasing textile has a determinable length, girth and depth of non-perforated fibrous material which can be prepared to meet specific shapes, sizes and thicknesses of solid matter;

(iii) Each agent-releasing textile can be employed either as a configured tubular conduit whose internal lumen is usefully employed for the conveyance of fluids in-situ, or, alternatively, as a solid mass of nanofibrous material which achieves its intended purpose without regard to or actual use of the internal lumen then existing within the textile fabric.

By definitional requirement, the agent-releasing nanofibrous textile (optionally also the antecedent forerunner of each subsequently generated medical article or device) is a non-woven material comprised of discrete fibers. The nanofibrous composite material forming the textile fabric has been electrospun from a liquid admixture and blending in a liquid organic carrier of at least two different materials: a synthetic substance and a biologically active agent. This admixture of two diverse chemical compositions can be prepared in a wide range of varying ratios using a liquid organic carrier, followed by application of an electric current to create the biocomposite material To illustrate the range and variety of compositions deemed suitable for use as a blended mixture, a listing of suitable synthetic substances is presented by Table 1 below. It will be noted that the listing of Table 1 presents some exemplary synthetic substances long deemed suitable for use as synthetic fibers. To complete the description. Table 2 lists some of the typical and more commonly available organic liquids which can be usefully employed alone and/or in blends as the liquid carriers.

TABLE 1

| Illustrative Synthetic Substance |
|---|
| Polymeric Fibers |
| polyethylene terephthalate; polybutylene terephthalate; polytrimethylene terephthlate |
| Polyurethane; |
| polyglycolic acid; |
| polyamides, including nylons and aramids; |
| Polytetrafluoroethylene; and |
| mixtures of these substances |
| Other synthetic fiber compositions (using TFPIA generic fiber names) |
| Acetate; |
| Triacetate; |
| Acrylic; |
| Modacrylic; |
| Olefin (Polypropylene, polyethylene, and other polyolefins); |
| saran |

TABLE 2

Representative Organic Liquid Carriers

Hexafluoroisopropanol;
Dimethylformamide;
Dimethylsulfoxide;
Acetonitrile;
Acetone;
Hexamethylphosphoric triamide;
N,N-diethylacetamine;
N-methylpyrrolidinone;
Ethanol;
4-methylmorpholine-N-oxide monohydrate At least some of the fibers comprising the textile fabric will demonstrate a range of properties and characteristics, as follows.

1. The fibers constituting the agent-releasing textile (and the subsequently generated medical article or device) will have a demonstrable capacity to take up water and/or aqueous liquids and/or organic liquids and/or organic based liquids (with or without direct wetting of the fibrous material). The mode or mechanism of action by which organic and aqueous fluids are taken up by the fibers of the textile (and/or become wetted by the fluid) is technically insignificant and functionally meaningless.

Thus, among the different possibilities of fluid (aqueous and/or organic) uptake are the individual alternatives of: absorption; adsorption; cohesion; adhesion; covalent bonding; non-covalent bonding; hydrogen bonding; miscible envelopment; molecule entrapment; solution-uptake between fibers; fiber wetting; as well as others well documented in the scientific literature. Any and/or all of these may contribute to organic and/or aqueous fluid uptake in whole or in part. Which mechanism of action among these is actively in effect in any instance or embodiment is irrelevant.

2. By choosing a particular chemical formulation and/or desired stereoscopic (or three-dimensional) structure for the synthetic substance of the fabrication, the resulting biologically active textile can be prepared as a fabric having a markedly long functional duration and lifespan for in-vivo use. Accordingly, by choosing one or more durable and highly resilient chemical compositions as the fibers of choice, textiles effective for many years' duration and utility may be routinely made. All of these choices and alternatives are conventionally known and commonly used today by practitioners in this field.

It is also well recognized that some synthetic chemical compositions are available in a range of diverse formulations. As one example of a highly resistant chemical composition having many alternative formulations are the polyethylene terephthalates, of which one particular formulation is sold under the trademark DACRON.

As is commonly known in this field, a range of differently formulated polyethylene terephthalates (or "PETs") are known to exist and are commercially available, each of these alternatives having a different intrinsic viscosity [or "IV", as measured in o-chlorophenol or "OCP", at 25° C.]. Typically, these differently formulated polyethylene terephthalate compounds can vary from less than 0.6 dl/g [IV] to greater than 1 dl/g [IV]; yet each of these alternative polyethylene terephthalate formulations can be dissolved in ice-cold 100% hexafluoroisopropanol. Thus, the electrospinning of appropriately prepared HFIP solutions containing any of such alternatively formulated polyethylene terephthalates will result in the fabrication of nanofibrous textile fabrics which are capable of independent or combined release of many diverse drugs, proteins and genetic materials.

3. The fibers comprising the agent-releasing textile (and the subsequently generated medical article or device) can be prepared in a variety of organizations as a tangible structure. Thus, as conventionally recognized within the textile industry, the textile fabric may vary in size or thickness; and may optionally receive one or more interior and/or exterior surface treatments to enhance particular attributes such as increased in-vivo biocompatibility or a greater expected time for functional operation and use in-vivo. All of these organizational variances are deemed to be routine matters which will be optionally chosen and desirably used to meet particular medical needs or individual patient requirements.

4. The fibers comprising the agent-releasing textile (and the subsequently generated medical articles or devices) can be prepared to meet the particulars of the intended in-vivo medical use circumstances or the contingencies of the envisioned clinical/therapeutic application. Thus, the textile fabric can alternatively be prepared either as a relatively thin-walled biocomposite, or alternatively as a thick-walled material; be produced as an elongated object having a diverse range of different outer diameter and inner diameter sizes; and be fashioned as a relatively inflexible or unyielding item or as a very flexible and easily contorted length of matter.

B. The Choosing of an Appropriate Biologically Active Agent

A number of different biologically active agents can be beneficially and advantageously utilized in tandem with the nanofibrous textile fabric. However, there are several minimal requirements and qualifications which the biologically active molecule-whatever its particular composition and formulation as a chemical compound, composition or molecule-must demonstrably provide in order to be suitable for use in the present invention. These are:

(i) The chosen agent must be capable of demonstrating its characteristic biological activity before becoming temporarily bound to and immobilized by the material substance of the fabricated textile. This characteristic biological activity must be well recognized and will constitute its ability/capacity to function as an active mediator in-situ.

(ii) The particular agent immobilized upon or within the material substance of the textile fabric must be capable of demonstrating its characteristic biological activity (its mediating capacity) after becoming immobilized and bound; and (iii) The immobilized agent bound into the material substance of the textile fabric will be released in-situ from the non-biodegradable polymer and be delivered into the surrounding local environment as a freely mobile molecule which retains its characteristic biological activity (its mediating capacity) over an extended period of time after the agent-releasing textile has been utilized in-vivo and allowed to take up water.

In addition, since the primary medical application for the fabricated textile is expected to differ and vary extensively from one embodiment to another, it is intended that the characteristic biological properties of the chosen agent serve to aid, promote, and/or protect the naturally occurring pathways and processes of the body which occur in-vivo.

Accordingly, it is deemed likely that the primary function and capabilities of the chosen biologically active molecule will differ and vary in many instances; and thus there are multiple purposes and a range of individual goals for the releasable substance, among which are the following: (1) to serve as an antimicrobial agent—i.e., as an anti-bacterial or anti-fungal composition having a broad or narrow spectrum of activity; (2) to function as an anti-neoplastic compound effective against specific kinds of tumors; (3) to operate as a selective physiological aid—i.e., as a mediator which serves to avoid vascular complications such as blood coagulation or acts to prevent the formation of blood clots; and (4) to act as a pharmacological composition—i.e., as a drug or pharmaceutical which deactivates specific types of cells and/or functions to suppress or inhibit a variety of different humoral and cellular responses associated with or related to inflammation and the inflammatory response in-vivo. Examples of each are presented hereinafter.

The Unique Electrospinning Perfusion Method of Manufacture

The Generation of Nanofibrous Tubular Structures

A preferred method for making the agent-releasing textile of the present invention is via the unique technique of electrospinning perfusion. For this purpose, an electrospinning perfusion assembly is erected which comprises, at a minimum, a rotating mandrel with a target surface which can be set at a pre-selected rotation speed; a needle fronted perfusion instrument with a spinerette, such as a syringe, which can be set to deliver a liquid mixture at a pre-specified flow rate; an electrical coupling for controlling and coordinating the electrical voltage applied across the perfusion needle and which is grounded to the rotating mandrel; and a controllable supply of electrical power.

An admixture is prepared comprising a chosen non-biodegradable material and a biologically active agent of choice. These components are blended together into an organic liquid carrier. In one embodiment, the organic liquid carrier is cooled to an ice-cold (e.g. about 4° C.) temperature. For reasons that are not clear, this cooling step facilities the proper formation of the admixture and speeds the dissolution of the non-biodegradable material. For example, one preferred liquid admixture or blending is obtained by combining 20% w:v polyethylene terephthalate (PET) with 1.5% w:v of an antimicrobial (e.g., Cipro or Diflucan), or with 1.5% w:v of an anti-neoplastic compound (e.g., Paclitaxel, Everolimus, Sirolimus), in a sufficient quantity of ice-cold hexafluoroisopropanol (hereinafter "HFIP"). The resulting admixture is subsequently loaded into the electrospinning perfusion assembly.

For example, a 10 ml syringe with a stainless steel 18-gauge blunt spinneret (0.5 mm internal diameter) is then filled with the liquid polymer blending and placed onto a Harvard Apparatus syringe pump for subsequent perfusion. Perfusion is the action and the act of causing a liquid or other fluid to pass across the external surfaces of, or to permeate through, the substance of a tangible entity or a configured physical construct. Perfusion of a liquid or fluid thus includes the alternative actions of: a sprinkling, pouring, or diffusing through or overlaying action; a covering, spreading, penetrating or saturating action (termed "suffusion"); a slow injection or other gradual introduction of fluid into a configured space or sized internal volume (termed "infusion"); and a passage across a surface or through a discrete surface or tangible thickness of matter, regardless of the mechanism or manner of transfer employed for such fluid passage.

Once the admixture has been properly loaded, the electrical coupling and syringe pump are activated and the admixture is electrospun onto the target surface. In one embodiment, the step of electrospinning is carried out at a temperature which does not harm the biological activity of the biologically-active agent in the admixture. The reaction temperature is, in one embodiment, ambient room temperature (20-25° C.), but when necessary or desired can be chosen to be within a temperature reaction range of about 0-50° C.

Utilization of this assembly permits uniform coating of the liquid admixture onto the surface of the mandrel; and the applied electrical voltage can be varied as needed to control the formation of the nanofibers upon the mandrel's surface.

It will be recognized in particular that electrospinning over a broad range of conditions Is possible for polyesters. Thus, a range of differently formulated polyethylene terephthalates (or "PETs") of intrinsic viscosity [or "IV" as measured in OCP at 25° C.] that range from less than 0.6 dl/g [IV] to greater than 1 dl/g [IV] can be dissolved in ice-cold 100% hexafluoroisopropanol. Electrospinning appropriately prepared HFIP solutions of such polyethylene terephthalates results in the fabrication of nanofibrous textile fabrics capable of independent or combined release of diverse drugs, proteins and genetic materials.

A Small Batch System

For fabricating small batches of product using this unique method, a chemically resistant syringe with a stainless steel blunt spinneret can serve as a functional instrument for perfusion. Alternatively, of course, any other tool, assembly or instrument capable of performing perfusion at a pre-selected flow rate and low reaction temperature can be usefully employed.

In this small batch system, the perfusion syringe of the assembly is filled with the prepared liquid mixture described above and placed onto a Harvard Apparatus syringe pump. The perfusion rate is preferably set at 3 ml/hour at 25° C. If desired, however, the flow rate can be increased and/or decreased to meet specific requirements. Similarly, the reaction temperature is preferably ambient room temperature (20-25° C.), but when necessary or desired can be chosen to be within a temperature reaction range of about 0-50° C.

A PTFE-coated stainless steel mandrel (diameter ranges=0.75 mm-35 mm) is preferably set at a jet gap distance of 15 cm from the tip of the syringe needle. Gap distance can be varied at will to change the fiber diameter size. The rotatable mandrel was then electrically grounded to the power source, with the positive high potential source connected to the syringe needle. The mandrel rotates or spins at a pre-selected rate of rotation throughout the act of liquid perfusion.

Perfusion

Perfusion of the polymer solution begins upon application of the electric current to the tip of the syringe needle (typically 15 kV), which then moves at a preset constant speed and fixed distance from the mandrel surface for a limited time period (typically about 40-90 minutes in duration). This process of manufacture is therefore termed "electrospinning perfusion"; and yields a fully fabricated, elongated nanofibrous textile conduit whose inner diameter size corresponds to the overall diameter of the mandrel (in this instance, 4 mm).

When using a single nozzle (or syringe needle), it was that increasing electrospinning time significantly beyond about 40 minutes increased the rigidity of the resulting nPET material. However, multiple nozzles (or syringe needles) can be used concurrently to reduce the time required to fabricate tubular structures of the appropriate rigidity. The use of multiple injection streams to Increase production rates is a familiar concept to those skilled in the art; and, accordingly, the use of multiple nozzles lies within the scope of the present invention.

Optional Follow-Up Processing

When the process is used to make certain kinds of medical articles such as synthetic vascular graft prostheses, a crimping procedure is employed as an optional, but very desirable, follow-up process. Accordingly, after being formed as a hollow tube by electrospinning perfusion, the thickness and girth of the originally formed fibrous composite wall and exterior surface preferably is then intentionally altered into a crimped structural form via a limited heat (low temperature) set technique, followed by compression of the fibrous composite wall, in order to provide kink-resistance for the elongated tube.

In brief, the end portions of the formed hollow tube (appearing about 1 cm from each end of the mandrel) are cut off and discarded. The remainder of the elongated hollow tube is then stretched 25% of the starting segment size while on the mandrel in order to provide a set strain across the fibers, a manipulation that occurs in normal fiber extrusion. The stretched tubes are then immediately exposed to 100% ethanol for 2 hours time at room temperature (or in 100% ethanol for 30 minutes with sonication) in order to remove the residual solvent, followed by air-drying overnight at room temperature. This crimping technique permits a user to form specific shapes (e.g. bends, etc) in the fabric without using high-temperature melt techniques which would damage the biologically-active agent.

The Generation of Flat Sheet Nanofibrous Textile Fabrics

Similar in its essentials to the technique described above. DACRON chips were dissolved in ice-cold 100% hexafluoroisopropanol (19% w:v) and mixed on an inversion mixer for 48 hours in order completely solubilize/e the chips. The self-contained, semi-automated electrospinning apparatus containing a Glassman power supply, a Harvard Apparatus syringe pump, an elevated holding rack, a modified polyethylene chamber, a spray head with power attachment and a reciprocating system was again used.

The stirrer was used to provide a holding chamber for the new flat collecting plate employed to generate a sheet format. The design of this surface is based upon the collecting plate employed by Li et. al. [see Li W J, Laurencin C T, Caterson E J, Tuan R S, Ko F K., "Electrospun nanofibrous structure: A novel scaffold for tissue engineering". J Biomed Mater Res 60:613 (2002)]. In short, a flat 12 cm.times.10 cm copper plate, containing a 6 cm stainless steel rod extending from the underside of the plate was designed and grounded to the power source.

A 10 ml chemical-resistant syringe was filled with the polymer liquid. A stainless steel 18-gauge blunt spinneret (0.5 mm internal diameter) was then cut in half, with the syringe fitting end connected to the polymer-filled syringe. Nalgene PVC tubing was connected to the syringe filled with the polymer solution followed by connection to the other half of the blunt spinneret within the spray head. The line was then purged of air, with the syringe then placed onto the syringe pump. The high potential source was connected to the spray head tip, with the plate set at a jet gap distance of 15 cm from the tip of the needle. The perfusion rate was set at 3 ml/hour at 25° C.

Perfusion of the polymer liquid was started upon application of the current to the tip of the needle (15 kV) with electrospinning proceeding for 1 hour and 40 minutes, with rotation of the plate 20 degrees every 20 minutes. This resulted in a flat, planar sheet of nanofibrous textile material being formed.

The agent releasable nanofibrous textile formed by the electrospinning method described above has a number of unique structural features which are the direct result and characteristic of its unique mode and manner of manufacture.

1. The agent-releasing textile fabricated via one of the two different electrospinning perfusion techniques will yield a discrete tubular article of fixed inner-wall and outer wall diameters, and a solid wall girth and configuration formed of a nanofibrous composite composition. The material substance of the fabricated wall typically shows that the synthetic substance is present as discrete fibers about $10^{-8}$ meters in diameter size. The fiber size is clearly demonstrated by the empirical data presented subsequently herein.

2. The interior wall surface and the exterior wall surface of the tubular structure comprising the agent-releasing textile are markedly different owing to the crimping and heat setting treatments following the initial electrospinning perfusion steps of the methodology. Thus, the exterior wall surface can possess a crimped and a somewhat irregular appearance. In comparison, the interior wall surface and the internal lumen of the conduit as a whole presents a smooth, regular, and even appearance which is devoid of perceptible projections, lumps, indentations, and, roughness.

3. The nanofibrous composite material substance of the textile fabric, whether existing in tubular structure form or in planar sheet form, is resilient and can be prepared in advance to provide varying degrees of flexibility, springiness, suppleness, and elasticity. Moreover, the nanofibrous biocomposite wall is durable and strong; is hard to tear, cut, or breakup; and is hard-wearing and serviceable for many years' duration.

4. The nanofibrous material substance of the agent releasable textile, whether present in tubular structure form or in planar sheet form, is biocompatible with the cells, tissues and organs of a living subject; and can be implanted surgically in-vivo without initialing or inducing a major immune response by the living host recipient. While aseptic surgical technique and proper care against casual infection during and after surgery must be exercised, the agent releasable textile can be usefully employed for a variety of applications in-vivo.

The Major Benefits and Advantages of the Electrospinning Perfusion Techniques

The electrospinning perfusion technique-whether employed to fabricate tubular structures or flat sheets, has a number of advantages over conventionally known manufacturing processes. These include the following:

A first benefit is dial no exogenous binders, cross-linking compounds, or functional agents are required by the process either to form the substance of the fabric or to maintain the integrity of the fabricated textile. The synthetic substance prepared in liquid organic solvent can be generated directly into nanofibrous fabric form via the low reaction temperatures (typically ranging between 0-50° C.) permitted and used by the electrospinning perfusion process. In addition, the nanofibers of the fabric act to seal the interstices of the composite material; therefore, no sealants as such are required. This manufacturing technique also benefits the manufacturer in that the technology is not a dipping or immersion method of preparation, which can be awkward and difficult to perform; or is a process which typically requires the addition of heat, such as if a conventional melt spinning method of fiber formation were employed.

A second benefit is that the electrospinning perfusion technique yields a textile fabric formed as a nanofibrous composite in which the fibers (e.g., PET) exist independently and are visibly evident throughout the material of the textile. This structural distribution of discrete fibers within the fabric adds strength and flexibility to the textile as a whole. Also, the presence of these fibers collectively provides sites into which diverse biological agents (such as antimicrobials, anti-neoplastic agents, and the like) can be temporarily incorporated and indefinitely, although non-permanently, immobilized until such time as the textile takes up fluid—i.e., any aqueous and/or organic liquid.

A third benefit is the capability for direct incorporation of biologically-active agents onto the nanofibrous material, whatever its final shape and structure. This process holds several key advantages over other conventionally known methodologies in that:

The active agent is incorporated into the fabricated nanofibrous material without molecular modification, and is non-permanently immobilized within each individual fiber surface as the individual fibers are formed.

No one particular mechanism of incorporation is responsible for the active agent becoming non-permanently immobilized within each individual fiber of the fabricated nanofibrous material; and thus any and all of the commonly known mechanisms—such as absorption, adsorption, polarity, ion attraction, and the like—may be involved.

The amount of active agent can be adjusted within the bulk polymer depending on the specific or intended application.

No cross linking agents are needed, or used, or desired at all, thereby avoiding concerns over drug carrier toxicity, biocompatibility, and mutagenicity.

Low reaction temperatures are used during the fiber/fabric formation procedure, thus maintaining the biologic activity of the active agent.

Active agent elution from the textile fabric is controlled and sustained over time, as shown in the experimental studies and empirical data presented hereinafter.

The Releasable Anti-Neoplastic/Anti-Prolerative Agents

Figure 3:
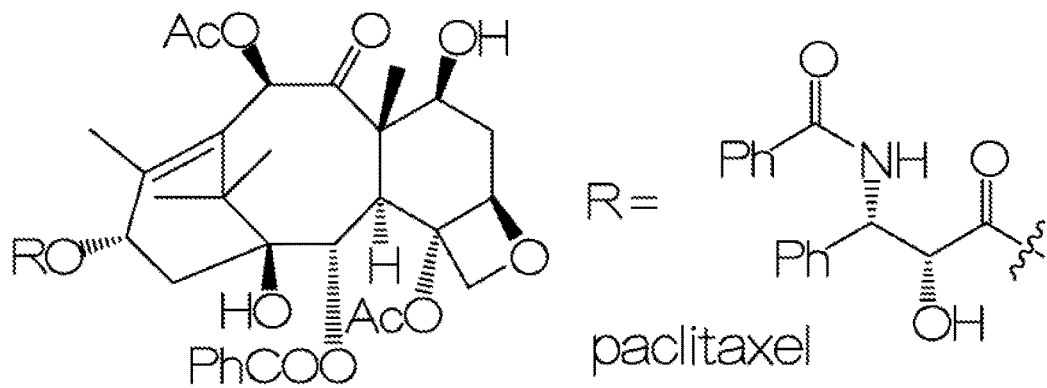
FIG. 3 is an illustration of the chemical structure of Paclitaxel.

Paclitaxel, also known as Taxol, a diterpenoid-structured molecule shown by FIG. 3, is a potent anti-neoplastic agent. Paclitaxel has been shown to inhibit vascular smooth muscle cell (VSMC) proliferation, migration and inflammation. Additionally, Paclitaxel has been shown to inhibit the secretion of extracellular matrix by VSMCs, a major component of neointima formation leading to vessel restenosis. Paclitaxel stabilizes and enhances assembly of polymerized microtubules, an important component of the cytoskeleton involved in cell division, cell motility and cell shape. Other examples of anti-proliferative/anti-neoplastic agents such as Sirolimus, Everolimus, Tacrolimus, 5-FU, daunomycin, mitomycin and dexamethasone can also be used.

Additionally, microtubules are involved in signal transduction, intracellular transport and gene activation. Paclitaxel has shown promise as a treatment for various types of cancers as well as for the prevention of restenosis following stent placement.

Nevertheless, when Paclitaxel is incorporated into a hydrophobic carrier polymer coated onto a metallic stent, it elutes for only 10-14 days. Other research groups have attempted to incorporate Paclitaxel into biodegradable polymers that would comprise the stent. However. Paclitaxel activity was significantly reduced due to the melt extrusion process for the fibers.

This issue would not be a problem with the present invention due to the low temperature formation of the nanofibrous polyethylene terephthalate (PET) fibers. Therefore, the fabrication of a nanofibrous polyethylene terephthalate (PET) material with a slow-releasing anti-neoplastic agent such as Paclitaxel would be particularly effective and medically applicable to endovascular stents and prosthetic vascular grafts, both of which currently experience neointimal hyperplasia. Additional examples of other active anti-neoplastic agents suitable for use in the present invention include Rapamycin and Dexamethasone.

The Fluoroquinolone Antibiotics

Antibiotics vary in structural type, spectrum of activity, and clinical usefulness. Fluoroquinolones such as Ciprofloxacin (hereinafter "Cipro") are shown structurally by FIG. 1, and are of particular use and value in this invention. Quinolone antibiotics are chemically stable, and effective at tow concentrations against the common clinically encountered organisms, particularly those bacteria responsible for biomaterial infection. These antibiotics also have structural features (solubility, molecular mass, and functional groups) that coincide with those of textile dyes known to have interactions with polyethylene terephthalares.

This family of antibiotics has expanded considerably—Ciprofloxacin, Ofloxacin, Norfloxacin, Sparfloxacin, Tomafloxacin, Enofloxacin, Lovafloxacin, Lomefloxacin, Pefloxacin, Fleroxacin, Avefloxin, Levofloxavin, Moxifloxacin and DU6859a; and the fluoroquinolone family as a whole has become the drug of choice for many applications. These antibiotics are effective at low concentrations; and hold an ideal antimicrobial spectrum against microorganisms most commonly encountered clinically in wound infection, with significant activity against many relevant pathogens-such as *S. aureus*, methicillin-resistant *S. aureus, S. epidermidis, Pseudomonas* species, and *Escherichia coli*. Moreover, Fluoroquinolones are heat stable; are of 300-400 r.m.m.; and have many structural features analogous to dyes. Accordingly, this family of antibiotics possesses those characteristics which are highly desired for use with the present invention.

A list of some representative antimicrobial/antiseptic agents that can be used solely or in conjunction with the fluoroquinolones is includes β-lactams, biguanides cephalosporins, chloramphenicol, macrolides, aminoglycosides, quaternary ammonium salts, tetracyclines, sulfur-containing antimicrobials, silver-containing compounds, bis-phenols (triclosan), vancomycin, novobiocin and steroids (fusidic acid)

The Anti-Fungal Agents

Figure 2:
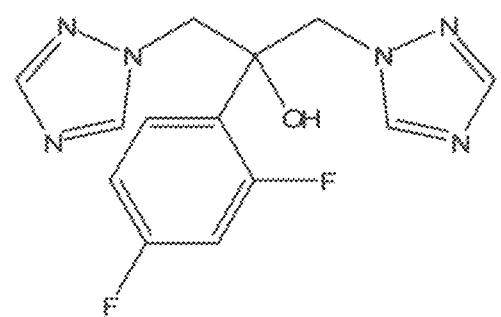
FIG. 2 is an illustration of the chemical structure of Diflucan.

Development of antifungal agents has been on the rise over the past two decades due to a significant increase of superficial (i.e. nail beds) and invasive (i.e. blood-borne and medical-device related) infections. Fluconazole, known as Diflucan, a triazole-structured antifungal agent introduced in early 1990 and structurally shown by FIG. 2, has emerged as one of the primary treatments for *Candida* infections. The mode of action of Diflucan is the inhibition of 14.alpha.-lanosterol demethylase in the ergosterol biosynthetic pathway, and results in the accumulation of lanosterol and toxic 14.alpha.-methylated sterols in the fungal membrane. Similar to the selection of Cipro. Diflucan has structural features (solubility, molecular mass, and functional groups) that coincide with those of textile dyes known to have interactions with polyethylene terephthalate fibers. A agent-releasing textile combining polyethylene terephthalate with a slow-releasing antifungal agent such as Diflucan will have a marked impact on topical and implantable biomaterials such as medicated pads (useful for nail bed and skin infections), tampons (using localized release for yeast infection) and catheter cuffs.

Other examples of anti-fungal agents typically will include amphotericin B, Nystatin, Terbinafine, Voriconazole, Echinocandin B and Itraconazole The Antimicrobial Peptides A novel class of antimicrobial agents known as antimicrobial peptides (or "AMPs") has been discovered during the past two decades. These "natural" antimicrobial agents, which consist of a large number of low molecular weight compounds, have been discovered in plants, insects, fish and mammals, including humans [see for example. Marshall S H & Arenas G., "Antimicrobial peptides: A natural alternative to chemical antibiotics and a potential for applied biotechnology", J Biotech 6(2): 1(2003)]. These peptides, whose composition can range front 6-50 amino acids, have been shown to have an important role in innate immunity. There are 5 general classifications for AMPs [see for example, Sarmafilk A., "Antimicrobial peptides: A potential therapeutic alternative for the treatment of fish diseases", Turk J Biol 26:201(2002)], which are based on the three-dimensional structure of the peptide as well as the biochemical characteristics. These groups consist of: (1) linear peptides without cysteine residues or hinge region; (2) linear peptides without cysteine residues and a high proportion of certain amino acids; (3) antimicrobial peptides with one disulfite bonds that form a loop structure; (4) antimicrobial peptides with two or more disulfite bonds; and (5) antimicrobial peptides that have been derived from other larger proteins via post-translational processing.

AMPs have shown broad spectrum antimicrobial activity against both gram-positive (i.e., *Staphylococcus aureus* and *epidermidis*) and negative (i.e., *Pseudomonas aeruginosa, E. coli*) bacteria. Some AMPs have also been shown to be effective against fungus [see for example. De Lucca A. J., "Antifungal peptides: Potential candidates for the treatment of fungal infections", Expert Op Invest Drugs 9(2):273 (2000); and Selitrennikoff C P, "Antifungal proteins", Appl Environ Microbiol 67(7):2883 (2001) and several antibiotic-resistant bacteria such as *Mycobacterium tuberculosis* [see for example, Linde C M A, Hoffier S E, Refai E, Andersson M., "In vitro activity of PR-39, a proline-arginine-rich peptide, against susceptible and multi-drug resistant *Mycobacterium tuberculosis*", J Antimicrob Chemother 47:575 (2001); Miyakawa Y, Ratnakar P, Rao A G, Costello M L, Mathieu-Costello O, Lehrer R I, Catanzaro, A., "In vitro activity of the antimicrobial peptides human and rabbit defensins and porcine leukocyte protegrin against *Mycobacterium tuberculosis*". Infect Immun 64(3):926 (1996); and Sharma S, Verma I, Khuller G K, "Therapeutic potential of human neutrophil peptide 1 against experimental tuberculosis", Antimicrob Agents Chemother 45(2):639 (2001)].

Although the mode of action by these peptides has not been fully elucidated, it is postulated that many of these peptides interact directly with the bacteria wall, creating small channels (pores) which causes membrane destabilization, thereby depleting the bacteria of its cytoplasmic content [see for example, Matsuzaki K., "Why and how peptide-lipid interaction utilized for self defense? Magainins and tachyplesins as archetypes", Biochemica Biophys Acta 1462 (1-2):456 (1999)]. While effective against bacteria walls, there appears to be limited affinity for eukaryotic cells possibly due to the different composition and net charge of the membranes. Several AMPs (i.e., Nisin and Daptomycin) have been recently approved by the FDA for commercial and medical markets. This acceptance paves the way for utilizing other AMPs such as pleurocidin. Additionally, federal standard testing procedures, which were used to provide safety and efficacy data for these AMPs, have been established. Other representative types of AMPs include Cationic peptides such that Cecropins, Defensins, Thionins, Amino Acid-Enriched Histone-Derived Beta-Hairpin and other Natural and Functional Proteins. Further examples of anionic peptides include Aspartic Acid-Rich, Aromatic Dipeptides and Oxygen-Binding Proteins.

The Analgesic Agents

Analgesic agents are widely used in human and veterinary medicine in order to prevent inflammation, thereby reducing pain and other symptoms such as itching and swelling. These agents have structural properties that are comparable to standard textile dyes such as molecular weight, functional groups and benzene-ring based composition. Exemplifying such analgesic agents are Diphenhydramine Hydrochloride. Meloxicam, Hydrocortisone Acetate, Pramoxine Hydrochloride, Lidocaine and Benzocaine.

The Anti-Viral Agents

Antiviral agents have been used to combat viral infections ranging from the flu to HIV infection and organ transplant rejection. Examples of some antiviral agents include Oseltamivir (Flu), Zanamivir (Flu), Saquinavir (HIV), Ritonavir (HIV), Interferon (HIV/Implant Rejection).

Other Classes of Suitable Biologically Active Agents

A number of other classes of biologically active agents can also be used in the agent releasable textile. All of these choices are biochemical mediators which can be initially immobilized via the electrospinning technique without serious deterioration, and then subsequently released from the nanofibrous textile fabric upon uptake of water. Representative examples of such classes comprising additional suitable biologically active agents are presented by Tables 9, 10, and 11 of U.S. Publication no. 2006/0200232A1, the content of which is incorporated by reference.

The Medical Articles Fashioned from the Agent Releasable Textile

It is expected and envisioned that each agent-releasing textile can be employed in the alternative either (1) as a configured tubular conduit whose internal lumen is usefully employed for the conveyance of fluids in-situ; or (2) as a solid mass of flat or planar nanofibrous sheet fabric which achieves its intended purpose without regard to or actual use of any internal lumen within the textile fabric. Some representative examples of the tubular format include vascular articles such as arterial vascular grafts; venous vascular grafts; prostheses for aneurysms; liners and covers for stents (coronary or endovascular) as well as non-vascular devices including catheter cuffs and coating for wires for transdermal devices (pacemaker leads). Illustrative examples of flat sheet formats include wound dressings such as treatment dressings, films, and/or sheets; gauze pads; absorbent sponges; bandages; and sewing cuffs. Further examples include transdermal release patches such as infection treatment; skin tumor treatments; and finger/toenail treatment.

Further examples include personal hygiene products such as tampons; and contraceptive delivery.

Some Intended Clinical/Therapeutic Applications for the Invention

The kinds of clinical/therapeutic applications for the prepared medical articles and devices are intended to include major traumatic wounds caused by accident, negligence, or battlefield conditions; planned surgical incisions and invasive body surgical procedures performed under aseptic conditions; transcutaneous incisions and vascular openings for catheter insertion and blood vessel catheterization procedures; and other body penetrations and openings made for therapeutic and/or prophylactic purposes.

The medical articles provided by the present invention thus are intended and expected to be manufactured as pre-packaged and pre-sterilized textile fabric articles; be an item which can be prepared in advance, be stocked in multiples, and be stored indefinitely in a dry state without meaningful loss of biological function or efficacy; and serve effectively in the treatment of disease, disorders, and pathological conditions under many different clinical circumstances.

The medical articles should be manufactured and tailored in advance to meet a wide range of intended use circumstances or contingencies expected to be encountered in a particular situation. For this reason, the constructed textile article can and should alternatively be prepared as a thick cloth and as a thin gauze; as a solid-walled configured tube; and as a delicate film. Equally important, the resulting construct may take physical form either as a stiff, inflexible and unyielding mass or as a very flexible and supple layer; have a varied set of dimensions and girth; appear as both a geometrically symmetrical or asymmetrical configured fabric; and can exist even as a slender cord or string-like length of material.

Medically, the agent releasable textile articles of the present invention can be employed in-vivo in the following ways: topically or subtopically; transcutaneously, percutaneously, or subcutaneously; or internally within the body's interior; viscerally or Immorally; and applied to any kind of body cavity, body tissue or body organ without regard to anatomic site or location.

Experiments, Empirical Data, and Results

To demonstrate the merits and value of the present invention, a series of planned experiments and empirical data are presented below. It will be expressly understood, however, that the experiments described herein and the results provided below are merely the best evidence of the subject matter as a whole which is the present invention; and that the empirical data, while limited in content, is only illustrative of the scope of the present invention as envisioned and claimed.

An illustrative recitation and representative example of the present invention is the preferred manner and mode for practicing the methodology is also presented below as part of the experimental method. It will be expressly understood, however, that the recited steps and manipulations presented below are subject to major variances and marked changes in the procedural details; all of which are deemed to be routine and conventional in this field and may be altered at will to accommodate the needs or conveniences of the practitioner.

Commercial Applications

Medium and Small-Diameter Artificial Arteries

Problem: Peripheral arterial disease (PAD) is estimated to affect some 8-10 million people in the United States alone. For patients needing surgical intervention, there is currently no prosthetic vascular graft accepted for vascular reconstruction in the lower extremities. The number of patients requiring this procedure is projected to significantly grow over the next decade due to an aging population in conjunction with the earlier prevalence of diabetes and hypertension as a result of increasing obesity rates in the general population. An autologous vessel graft is the first and currently only accepted choice in most arterial grafting procedures for these anatomic areas. However, this situation becomes problematic when disease progression has occurred throughout the vasculature or when the patient has utilized all of the harvestable veins for other surgical procedures, thereby leaving no viable arterial graft alternative for the patient. These complications result in significant morbidity and mortality rates. The two most commonly used synthetic materials, polyethylene terephthalate (polyester or PET) and expanded polytetrafluoroethylene, have been used extensively over the last several decades for medium and large diameter grafts, but have failed when evaluated for use as small-diameter (<5 mm internal diameter) vascular prostheses. Various technologies have been developed to improve biocompatibility of prosthetic grafts. While several of these technologies have shown early promise, none have been fully-accepted as a viable alternative to autologous vessel for distal bypass surgery.

Composition to address problem: a copolymer polyester (combination of polyethylene terephthalate (PET) and polybutylene terephthalate (PBT)) and bioactive agents: Anticoagulant (recombinant hirudin or Argatroban), antiproliferative (paclitaxel, everolimus, sodium butyrate and/or silencing siRNA), growth promoting (vascular endothelial growth factor, fibroblast growth factor) and/or antimicrobials (antibiotics, antimicrobial peptides, naturally-occurring antimicrobial proteins). The shape is a straight tubular construct or tapered internal diameter; can also incorporate crimp or inner wall reinforcement to provide greater flexibility. Dimensions: 0.75 mm internal diameter and larger (>40 mm); length from 1 cm-60 cm.

Synthesis Procedure: A PET/PBT (17.5%/2% w:v) polymer solution (15 ml) was prepared in ice-cold HFIP and mixed for 48 hours. The PET/PBT polymer solution was then equally divided (5 ml/vial). One portion of the polymer solution was left unmodified, serving as the non-drug loaded polymer solution (control). One of each of the bioactive agents from the selected categories was added to the other respective polymer solutions after 3 days of mixing. These solutions were mixed for two additional days before electrospinning. These polymer solutions (control and drug-loaded) were each added to individual 5 ml syringes and electrospun separately for 45 minutes onto either a 4 mm diameter Teflon-coated stainless steel mandrel or tapered steel mandrel (6 mm-4 mm). Jet gap distance was set at 15 cm. Perfusion of the polymer (3 ml/hour) was initiated upon voltage application (+20 kV). Electrospun materials were cut in a longitudinal direction to form flat sheets. The electrospun tubular constructs (control and drug-loaded nPBT-PBT) were removed off of the mandrel, stretched 25% of the original length and post-treated to remove any residual solvent by sonication in 100% ethanol for 30 minutes followed by then sonication in distilled water for 2 minutes. Grafts were air-dried overnight at room temperature. Electrospun materials were sterilized via ethylene oxide (EtO) using an Anprolene Sterilizer (230% RH, 12 hour cycle).

Hemodialysis Access Graft

Problem: End-Stage Renal Disease (ESRD) is a disease affecting more than a half million Americans. Current gold standards for hemodialysis access, radial cephalic vein fistulas and autogenous saphenous veins, have significant problems associated with their use. Arteriovenous fistulas (AVFs) need a long time to heal before access (6 weeks to 6 months). Surgical time for autologous grafts is significantly increased as a result of harvesting the vein as well as treatment prior to implantation. Additionally, most patients do not have veins to utilize due to co-morbidity, prior harvesting for a surgery or the need to save the vessel for a different surgical procedure (e.g. coronary artery or distal bypass). Viable veins may also not be available due to disease progression. Lastly, primary patency rates for these autogenous grafts after two years of implantation is approximately 20%, although cumulative patency rates as high as 89% have been reported after surgical/pharmacological intervention.

Synthetic grafts made of ePTFE are the current standards for synthetic vascular access grafts. These grafts have (depending on the study) comparable or worse primary patency rates than autogenous grafts and, similar to autogenous grafts, take a significant time to heal (at least 2-4 weeks) thereby preventing instant hemodialysis access. These prosthetic alternatives are also relatively stiff compared to the native vessels and have issues related to infection. The other issues associated with ePTFE grafts are seroma formation and occlusion due to intimal hyperplasia. Various efforts to improve the patency through coatings (carbon coating), impregnations (fibroblast growth factors) and surface protein binding (heparin) have failed to improve overall long-term patency rates. To date, thrombosis, infection and the lack of early access via needle puncture are the biggest issues associated with ePTFE grafts. Grafts made of a composite material (Vectra™; Thoratec Lab Co., Pleasanton, Calif., USA) comprised of polyurethane, silicone and PET fibers (as reinforcement) have recently entered the market. The graft has the self-sealing property and healing behavior comparable to ePTFE grafts. Additionally. Vectra™ does not require a long healing time prior to the first puncture. However, the solid silicone film located within two layers of polyurethane in order to impart impermeability and self-sealing to the graft prevents complete healing of the graft. The high elasticity of the graft also causes kinking of the native vein resulting in stenosis.

Composition to address problem: a copolymer of polyethylene terephthalate (PET) and polyurethane (PU) and bioactive Agents: Anticoagulant (recombinant hirudin. Argatroban or Bivalirudin), antiproliferative (paclitaxel, everolimus, sodium bulyrate and/or silencing siRNA) and antimicrobials (antibiotics, antimicrobial peptides, naturally-occurring antimicrobial proteins) Shape: Straight tubular construct; incorporates crimp within mandrel to provide greater flexibility. Dimensions: 6-8 mm internal diameter and smaller, length from 20-80 cm.

Synthesis Procedure: A polymer solution (10% w:v, 30/70 PET/PU) in conjunction with antibiotic (Moxifloxacin), anticoagulant (recombinant hirudin or rHir) and anti-proliferative (Paclitaxel or Pac) (1.5%, 1% and 1% w:v, respectively) was prepared. This solution was diluted an additional 20% with HFIP and mixed for an additional 2 hours. Further HFIP dilution of the original polymer solution prevented any complications during graft synthesis while improving final electrospun material. This diluted solution was then electrospun onto Teflon-coated stainless steel mandrels with a spring loaded within the mandrel to create the crimped structure (40 cm length; 6.2 mm diameter), resulting in a graft with an internal diameter of 6 mm and a length of 25 cm. The graft was then post-treated to remove any residual solvent by sonication in 100% ethanol for 30 minutes followed by sonication in distilled water for 2 minutes. Grafts were then air-dried overnight at room temperature for 72 hours. BioAccess grafts were ethylene-oxide (EtO) sterilized using an Anprolene Sterilizer at BioSurfaces, Inc. (cycle time=12 hours, room temperature, humidified conditions).

Ventricular Assist Device Tubular Device

Problem: Heart failure affects over 4.7 million Americans, with 550,000 new cases diagnosed each year. Of these cases, approximately 50,000 to 100,000 patients are in late-stage heart failure with only 8% of these patients surviving two years without undergoing a heart transplant or implantation of a ventricular assist device (VAD). Although VADs have improved the quality of life for patients in late-stage heart failure, only 2,000 patients receive VADs each year due to the high morbidity- and mortality associated with these devices. VADs, similar to all medical devices implanted within the vasculature, are prone to two major complications: thrombosis/thromboembolic phenomenon and infection. The annual healthcare cost for this major disorder is estimated at $10 to $40 billion. Significantly reducing these adverse complications would shift VAD use from "bridge to transplant" to "destination therapy", increasing the potential market from the current $100 million annually to $2.5 billion. Development of this technology may also have application for other implantable devices such as hemodialysis access grafts as well as medium-bore prosthetic arterial grafts and sewing cuffs comprised of polyester, in which thrombosis and infection are associated with their use.

Composition to address problem: a copolymer polyester (combination of polyethylene terephthalate (PET) and polybutylene terephthalate (PBT)) and Bioactive Agents: Anticoagulant (recombinant hirudin, Argatroban or Bivalirudin) and antimicrobials (antibiotics, antimicrobial peptides, naturally-occurring antimicrobial proteins). Shape: Straight tubular construct; can also incorporate crimp or inner wall reinforcement to provide greater flexibility. Dimensions: 4 mm internal diameter and larger; length from 5 cm-60 cm.

Synthesis Procedure: Polyester (17.5% w:v PET and 2% w:v poly(butylene terephthalate) or PBT) polymer solutions were prepared in ice-cold 100% hexafluoroisopropanol (HFIP). This polymer solution was mixed on an inversion mixer for 48 hours in order completely solubilize both components. To this solution, rHir (1% w:v) and Cipro (1.5% w:v) was added and mixed an additional two days. The self-contained, semi-automated electrospinning apparatus described in the contract was employed. Utilization of this system permitted uniform coating of the polymer onto the PTFE-coated stainless steel mandrel (diameter=6 mm). The high potential source was connected to the spray head tip. The mandrel, set at a jet gap distance of 15 cm from the tip of the needle, was then grounded to the power source. The perfusion rate was set at 3 ml per hour at 25° C., with perfusion of the polymer started upon application of the current to the tip of the needle (+15 kV). Electrospinning time was increased from 60 minutes to 90 minutes in order to significantly increase wall thickness. After electrospinning, the end portions of the conduit (1 cm from each end of the mandrel) were cut off and discarded. The remaining graft was stretched 25% of the starting segment size while on the mandrel. Conduits were left on the mandrel and placed into 100% ethanol and sonicated for 30 minutes, followed by a sonication in sterile distilled water for 2 minutes in order to remove residual HFIP solvent. These BioSpun-VAD conduits were cut to length and ethylene oxide (EtO)-sterilized.

Sewing Cuff Ring (Heart Valve Repair and Artificial Heart Valve Attachment)

Problem: Cardiac valve repair or replacement is indicated when progression of degenerative disease or bacterial infection of the native valve results in valvular dysfunction, thereby impacting cardiac output Both procedures require the use of a woven or knitted polyester ring with an internal reinforcement (Teflon, silicone or metal) to either stabilize the native valve (annuloplasty ring) or to attach a prosthetic heart valve (sewing cuff). Bacterial infection (prosthetic valve endocarditis or PVE) is a major complication associated with implantation of these devices. Infection of these devices can emerge via two mechanisms. Nosocomial infection at the time of surgery or post-operatively occurs approximately 1-4% of all valves implanted, resulting in significant morbidity and mortality. Blood stream infections (bacteremia) seeded at the implantation site prior to surgery have been shown to also occur in approximately 33% of all PVE cases, with a mortality rate above 50% from this serious complication. Staphylococcus aureus (S, aureus) and epidermidis (S. epidermidis) as well as Streptococci are shown to be responsible for 25-50% of all valve infections. Perioperative parental antibiotics often fail to permeate the avascular spaces immediately around the biomaterial once pathogens have adhered. The health care cost associated with treating PVE is projected to be greater than $60,000 per patient, with the annual market for cardiac surgery devices projected to range from $700 million to $1.4 billion.

Overall, valvular disease affects 2.5% of the United States population (this percentage is higher in older age groups). Over 90,000 mechanical and bioprosthetic valves are implanted in the United States each year, with over 280,000 valves implanted worldwide. While the emergence of transcatheter heart valve therapy will reduce selection of these devices for certain procedures, overall valve use is still projected to increase due to an aging population and, to a lesser extent, a more aggressive surgical approach to mitral valve insufficiency. Additionally, higher incidences of obesity and diabetes are expected to increase these numbers drastically. Currently, there are no clinically available infection-resistant prosthetic valves or sewing cuffs/annuloplasty rings. Due to the inertness of prosthetic valves, these annuloplasty rings and sewing cuffs are logical targets to provide localized antimicrobial delivery.

Composition to address problem: Polymer: Combination of polyethylene terephthalate (PET) and polyurethane (PU), Bioactive Agents: Anticoagulant (recombinant hirudin, Argatroban or Bivalirudin) and antimicrobials (antibiotics, antimicrobial peptides, naturally-occurring antimicrobial proteins). Shape: Ring shaped device, thickness can be varied. Dimensions: 5-35 mm internal diameter.

Synthesis Procedure: The electrospun sewing cuff is a composite nanofibrous construct, involving electrospinning of two polymer solutions. For both control and drug-loaded sewing cuffs (BioCuffs), a 10% (w:v) PU polymer solution (Chronoflex C Polycarbonate Polyurethane; 80A Durometer) was prepared in ice-cold 100% HFIP. Another polymer solution of 17.5% (w:v) PET and 2% (w:v) PBT was also prepared in ice-cold 100% HFIP. Each solution was then mixed for 48 hours on an inversion mixer. These two solutions were then electrospun sequentially to form the nanofibrous control sewing cuff material. To synthesize drug-loaded sewing cuffs (BioCuffs), after mixing the polymer solutions for 48 hours, the volumes of both solutions were diluted by adding 50% more HFIP. Cipro (1.5% w:v) was then added to the diluted PET-PBT and PU solutions and both polymer solutions were mixed for an additional 24 hours before electrospinning. A gap distance of 15 cm was set from the needle port to the collecting surface, which was a 9.5 mm diameter zinc-plated steel mandrel with a roughened surface. This mandrel was rotated at a constant speed of 270 rpm. Perfusion of the PET-PBT polymer (3 ml/hour) was started upon application of the current to the needle (+20 kV), with electrospinning proceeding for 5 minutes in the case of the control BioCuffs, or for 7.5 minutes in the case of the drug-loaded BioCuffs (1.5× duration for diluted polymer solution). Immediately after electrospinning the PBT-PBT layer, the Teflon tubing was connected to the PU-filled syringe and purged of residual polymer solution, with electrospinning of the PU layer proceeding for 15 minutes in the case of the control BioCuffs, or for 22.5 minutes in the case of the drug-loaded BioCuffs. After electrospinning both layers, the coated rods were washed in ethanol for 30 minutes with sonication, followed by a 2 minute sonication in distilled water to remove all traces of residual solvent. The edge of the material was rolled towards the opposite end of the rod, while measuring the thickness of the BioCuff with calipers when approaching the desired thickness of the final product. The material was then cut at the edge of the rolled sewing cuff. The detached cuff was rolled off the remainder of the rod length and the edge fused to complete cuff formation. Cuffs were air-dried at room temperature. Sewing cuffs, with and without drugs, were then sterilized by ethylene oxide (EtO) via an Anprolene Sterilizer (25° C., 10 psi, cycle time=12 hours). BioCuffs were then evaluated for surface fluorescence (Cipro) via a hand-held UV light and compared to control sewing cuffs.

Nanofibrous Bioactive Suture Materials

Cardiovascular disease (CVD) is the leading cause of death in the US, constituting over $272 billion of all national health expenditures. Most sequelae of CVD are confined to peripheral or coronary arteries, as blood vessels become occluded and require either surgical bypass procedures or percutaneous intervention (PCI) to restore blood flow to vital organs and limbs. As rates of obesity and diabetes climb to record levels each year, the prevalence of CVD continues to increase. By 2030, 41% of Americans will likely have some form of CVD. While PCI and drug eluting stents (DES) have become popular, recent studies show that bypass holds many advantages over PCI in terms of cost (due to the need for repeat PCI procedures), life expectancy, and quality of life for patients expected to live more than 2 years. The vast majority of recent studies comparing bypass grafts to stents corroborate this. Yet, bypass grafts still suffer early and late failure due to intimal hyperplasia (IH), the chronic excessive proliferation of smooth muscle cells (SMCs) as a response to injury of the blood vessel. In bypass grafts, IH occurs primarily at the anastomosis, where the suture joins the vein to the artery. Blood flow through the vein graft is gradually constricted by SMC overgrowth at the anastomosis until the vessel becomes occluded by thrombosis, causing 39% of bypass grafts to fail within 10 years and 50% to fail by 15 years. Harvesting and denuding are also known to cause a hyperproliferative response due to injury, but this response is acute and short-lived, and eventually regresses. IH occurs to a lesser degree at the floor of the native artery as well, where rerouted blood alters the natural hemodynamics of the vessel. However, this IH is an adaptation to a hemodynamic stagnation zone, and is thereby self-limiting once thickening at the floor of the artery incurs natural hemodynamic flow conditions. Alternatively, the presence of commercially used sutures generates a persistent, chronic hyperproliferative response that is the leading cause of failure in bypass grafts. Thus, controlling IH at anastomoses is our prime objective.

While antiproliferative DBS have improved revascularization rates by 55% compared to bare metal stents, sutures used for bypass grafts are yet 10 incorporate an antiproliferative drug eluting strategy. This is a major gap in the state of the art for vascular surgery, as bypass grafting is required in roughly 30% of all patients requiring coronary artery repair, and is firmly established as the best treatment option for patients with multi-vessel coronary artery disease and diabetes. The gold standard for sutures in vascular repair is polypropylene monofilament (Prolene®) or expanded polytetrafluoroethylene (ePTFE, Gore-Tex®) sutures. These sutures are stiff and structurally dissimilar to native tissue, with no ability to deliver a sustained dose of antiproliferatives. When a vein graft and artery are surgically joined via the clinically-favored "running" suture technique, there is a significant reduction in elasticity at the suture line, primarily due to the stiffness of industry sutures compared to the natural elasticity of the adjoining vessels. This stiffness is postulated to exacerbate IH through various mechanisms, suggesting there could be an improved healing response to a suture with better circumferential compliance (elasticity) at the suture line. Dissolvable sutures have also been developed for microvascular anastomoses, but the inherent loss of mechanical strength over time, increased cytotoxicity from degradation factors, and the risk of dislodged suture particles forming an embolism are too great to justify their study in a clinical setting. Alternatives to sutures have also been explored, but further work is needed before they are applicable for routine use.

To address the significant need to reduce IH in vascular suture repairs, we propose a suture that will: a) locally deliver a naturally occurring SMC-specific antiproliferative agent, b) better match the elasticity of the adjoining vessels, and c) encourage natural long-term healing due to its nanofibrous morphology.

Composition to address problem: Polymer, Polyester (combination of polyethylene terephthalate (PET) and polybutylene terephthalate (PBT)), polyurethane or combination of polyester and polyurethane; Bioactive Agents: Anticoagulant (recombinant hirudin or Argatroban), antiproliferative (paclitaxel, everolimus, sodium butyrate and/or silencing siRNA), growth promoting (vascular endothelial growth factor, fibroblast growth factor) and/or antimicrobials (antibiotics, antimicrobial peptides, naturally-occurring antimicrobial proteins); Shape: Yarn-like construct (nanofibrous single strand yarn); Dimensions: Thickness can be varied (0.025 mm-2 mm); length can be varied from 1m-2m. Can be made in a continuous fashion.

Synthesis Procedure: A polymer solution of 7% (w:v) polyurethane (cPU) and 3% (w:v) polyester (PTT; 0.63 dl/g) was prepared in HFIP and used to synthesize cPU-PTT control sutures. Another cPU-PTT solution containing 0.25% (w:v) Evero (LC Laboratories) was also prepared. Solutions were mixed for 48 hours prior to use. The collecting surface was a custom-designed apparatus consisting of a single 60 cm long, 0.75 mm diameter Teflon-coated flexible stainless steel mandrel, bent into a ring, grounded by a wire to the central axle, secured at both ends to a mechanized base to create a torus configuration. This device ensures an even coating onto the surface of the torus, while also creating alignment of polymer nanofibers in the toroidal/lengthwise direction of the electrospun coating. This collecting surface was inserted into a custom-designed, computer-automated electrospinning unit. Sutures were electrospun for 5 minutes using a 3 ml/hour flow rate. +20 kV applied voltage and 15 cm gap distance. After electrospinning, the tubular nanofibrous material was removed, manually twisted and elongated to its yield strain (300% of its original length) to create a suture. Each suture was then tightly coiled around a spool and placed into a vacuum oven (99.9% vacuum; 40° C., 24 hours). This process facilitates vaporization of residual HFIP while also increasing tensile strength as a result of cold working, annealing, and radially contracting the fibers.

Wound Dressing/Pak

Uncontrolled bleeding (hemorrhage) continues to be the leading cause of death upon deployment of military personnel in a theater of operations. Hemorrhage is also the second leading cause of death among civilian trauma deaths. These numbers have remained very high all throughout the history despite numerous advances in emergency treatment for severely injured military personnel and for civilian trauma cases. Studies indicate that more effective methods could have reduced mortality rates for our military personnel by at least one third. It is generally accepted that mortality-rates can be reduced considerably if the bleeding can be stopped within the first thirty-minutes of the trauma. As stated in the BAA "new materials and systems are required to advance the medical capabilities currently available, thereby reducing the amount of preventable battlefield deaths and reducing the effects resulting from injury."

Hemostatic devices were one of the treatments developed to reduce hemorrhage and save a soldier's lives. These devices are divided based on the application type into four categories 1) powders/granular agents, 2) solid materials, 3) flexible materials and 4) barrier agents or self-expanding gels. Powders are poured into the wounded areas and mostly work by absorbing fluids and low molecular weight products in the blood, thereby increasing the localized concentration of clotting factors and enhancing clot formation. The void remaining in technology for preventing wound hemorrhage on the battlefield is the rationale behind this BAA solicitation.

A light weight bioactive wound dressing/pack has been developed that provides the following characteristics: (1) Stop the bleeding quickly (2 minutes or less) and more efficiently at any point on the body (i.e. extremities or non-compressible wounds in the abdomen region) (2) Be easily applied by either a medic or by the wounded soldier themselves (3) Prevent wound infection resulting from a non-sterile environment via localized delivery of an antimicrobial agent (4) Provide direct pain-relief by controlled release of an analgesic agent (5) Be ready-to-use and requiring no special preparation/training (6) Be breathable to help wound healing and (7) Be stable under various climatic conditions for extended periods (−10° C. to 40° C.).

Composition to address problem: Polymer: Polyester (combination of polyethylene terephthalate (PET) and polybutylene terephthalate (PBT)), polyurethane or combination of polyester and polyurethane; Bioactive Agents: Coagulant (thrombin), antimicrobials (antibiotics, antimicrobial peptides, naturally-occurring antimicrobial proteins) and/or analgesic; Shape: Flat narrow material (dressing), rounded tampon shaped, or two flat electrospun materials joined together via ultrasonic welding or heat selling and containing super-absorbent polymer in the mid-portion; Dimensions: Variable width, length and thickness. In one embodiment, the width and length are each about 1 cm.

Synthesis Procedure: A nanofibrous bioactive hemostatic device prototype has been developed using electrospinning technology. Unlike any other hemostatic wound dressing present in the market, advanced wound dressing (AWD) has two components that work in a synergistic fashion to provide a multi-purpose hemostatic device. The first layer immediate to the wound contains an active agent that rapidly promotes blood clotting. The second layer has antibiotic and analgesics to ease pain, aid recovery and prevent harmful life threatening infections. The materials comprising these layers are made of polyester (PET). The PET polymer was selected due to its inertness, ease of electrospinning with drugs, ease of surface modification, soft feel, toughness and flexibility of the final electrospun product. The resulting electrospun PET material is non-toxic, porous (porosity=60%), nanofibrous (fiber diameter 300 nm to 3 vm), anisotropic (have same properties throughout), permeable (improves breathability) nonwoven structure with a very high surface area to volume ratio (improves the attachment of active moieties and enhances the contact interaction of injured tissue). These qualities are especially important for a wound dressing especially when dealing with non-linear, deep, incompressible wounds where the dressing needs to be packed into the wound. The blood-contacting layer is electrospun PET which is further mollified to create reactive groups along the surface of the nanofibrous layer. These functional groups are utilized to bind a potent coagulation enzyme onto the surface of the dressing. This pro-coagulant is adsorbed electrostatically onto the surface of surface-modified electrospun PET, stabilizing the coagulant for long-term storage. The coagulant is immediately released locally within the wound upon contact with blood providing rapid clot formation. Electrospinning also allows incorporation of selected drugs (antibiotic and analgesic agents) which help in the healing process. These not only retain their properties but also are released at a sustained rate as shown in benchtop assays. While the selected blood coagulant protein accelerates the wound clot formation, the antibiotic and analgesic agents prevent bacterial infection while casing wound pain, respectively. The AWD can be cut into different geometries to treat wounds of various types and locations just like standard gauze.

The coagulant is a proven non-immunogenic natural enzyme that directly activates the coagulation pathway as compared to other indirect coagulation drugs, chemicals or additives. The antimicrobial agent is a broad spectrum and third generation drug that is effective against a wide range of gram positive and gram negative bacteria encountered in the field under various combat scenarios. The analgesic agent is also a potent drug which is presently a part of the medic kit. This will be the first time to our knowledge that alt these agents will be delivered directly through a single hemostatic wound dressing.

Nanofibrous Stent Coating

Problem: Abnormal proliferation of neointimal smooth muscle cells (SMCs) is central to lesions of atherosclerosis and restenosis. Metallic stent devices, with either a bare metal surface (BMS) or drug-eluting surface (DES), have become widely utilized as a first option for patients with diseased blood vessels in which flow has been significantly restricted due to this proliferative event, thereby compromising organ or limb function. Stents are preferred over standard surgical interventions such as vessel bypass due to less invasiveness of the procedure and accelerated patient recovery times. Unfortunately, restenosis rates after BMS placement range from less than 10% to as high as 58%, a significant problem based on the 1.1 million stents annually implanted. Additionally, BMS have also been prone to late-term thrombosis and thromboembolism formation.

The advent of DES has reduced restenosis and stent thrombosis (ST) rates as compared to bare metal stents (BMS). While it was predicted that DES would overcome all of the complications associated with BMS, this has not come to fruition. The prevalence of these complications has stimulated the development of the next generation of drug-eluting stents which are bioresorbable (BRS). However, these studies are relatively short-term, with long-term efficacy still undetermined. Regardless of the overall design (BMS, DES or BRS), stent use still focuses on two specific criteria: 1) administration of systemic anti-platelet therapy and 2) delivery of a non-targeting anti-proliferative agent. Anti-platelet therapy is required in order to prevent thrombus formation on the stent until healing occurs. For anti-platelet therapy, a significant shift in the length of time for systemic anti-platelet therapy from 1 month minimum delivery to a now recommended minimum 1 year period has been implemented in order to drive down ST rates while attempting to allow healing to occur. This treatment is being carried out at a significant risk in hemorrhagic complications to the patient. Additionally, any deviation in anti-platelet therapy administration significantly increases the risk of ST. Delivery of anti-proliferative agents, while effective at preventing SMC proliferation, also affects endothelial cells, resulting in delayed re-endothelialization and vascular inflammation. This lack of complete healing increases the risk of thrombus formation, resulting in the need for long-term systemic anti-platelet therapy. Bioresorption of the BRS stent may eliminate the need for long-term anti-platelet therapy but issues with incomplete healing due to local delivery of these antiproliferative agents will still persist. Thus, there is a need to investigate alternative stent coating methodologies in which: 1) the effects of the treatments will persist for an extended period of time, 2) drug delivery can be targeted to specific areas within the vessel, 3) a combinatorial approach in terms of drug delivery can be used and 4) a scaffold for controlled vessel healing is provided.

Composition to address problem: Polymer: Polyester (combination of polyethylene terephthalate (PET) and polybutylene terephthalate (PBT)), polyurethane or combination of polyester and polyurethane; Bioactive Agents: Anticoagulant (recombinant hirudin or Argatroban), antiproliferative (paclitaxel, everolimus, sodium butyrate and/or silencing siRNA) and/or, growth promoting (vascular endothelial growth factor, fibroblast growth factor); Shape: Uniform thin coating of metallic stent; Dimensions: Thickness can be varied (0.05 mm-0.30 mm) as well as overall length.

Synthesis Procedure: A polyester (17.5% PET and 2% poly(butylene terephthalate) or PBT; w:v) polymer solution was prepared in ice-cold 100% hexafluoroisopropanol (HFIP) and mixed on an inversion mixer for 48 hours. This PET solution was then diluted 50% with HFIP, mixed for 1 hour and split in half. To one portion of this solution, 50 of DyLight 550 (DyLight; 10 mg/ml) was added and mixed for 1 hour on an inversion mixer. During this time, a 2 mm internal diameter metallic stent (Medtronic, Inc.) was slid onto a 2 mm Teflon-coated stainless steel mandrel. Both polymer solutions (with and without DyLight) were loaded into 5 ml syringes and placed onto our computer-automated electrospinning apparatus. The specific stent/mounting mandrel was set at a jet gap distance of 15 cm from the tip of the needle and the perfusion rate set at 3 ml per hour at 25° C. Perfusion of the polymer with DyLight was started upon application of the current (+15 kV) with electrospinning proceeding for 3 minutes. Perfusion of the unmodified PBT solution was begun immediately from another perfusion pump. This solution was electrospun for 5 minutes. Coated stents were then air-dried in a vacuum oven (600 mm Hg 37° C.) for 48 hours to remove residual HFIP.

Dermal Substitute/Artificial Skin Scaffold

Problem: Approximately 20% of cutaneous wounds with significant tissue loss transition into a non-healing or chronic state. Millions of individuals are impacted by pressure ulcers, including 600,000 patients whose wounds are secondary to venous insufficiency, and up to 3 million patients whose wounds result from immobility. The incidence of these types of chronic wounds, most prevalent in the elderly demographic, will likely increase as the average age of the population rises. The total cost of treating chronic wounds is estimated to exceed $8 billion annually, presenting a significant health care need. Beyond tissue damage, infection is the most prevalent complication in chronic and diabetic ulcers. Millions of clinical infection cases each year worldwide, contributing to thousands of deaths, are attributed to two species of bacteria, *Pseudomonas aeruginosa* and *Staphylococcus aureus*, The growing number of injuries and pathologies has significantly increased demand for wound management products.

A critical factor in preventing infection, scarring, and death from severe skin wounds is the prompt restoration of skin integrity. Split-thickness autografts are considered the "gold standard" for treating localized skin injuries, but the lack of available donor sites and donor site morbidity routinely hinder the recovery of patients with chronic wounds. Further, as the wound healing process has already been compromised in these patients with chronic wounds, autologous grafts may not be appropriate. While several composite skin and dermal substitutes have achieved some clinical success for restoring damaged skin, limited mechanical stability, sub-optimal wound healing, infection, scarring and prolonged healing times remain persistent problems. As such, there is a continued need for a dermal scaffold that promotes rapid tissue regeneration and vascularization (cellular ingrowth and angiogenesis), maintains the mechanical stability of the tissue, and provides barrier function (microbial resistance) for the wound site.

Composition to address Problem: Polymer: Top Layer=Polyester (combination of polyethylene terephthalate (PET) and polybutylene terephthalate (PBT)), polyurethane or combination of polyester and poly urethane. Bottom Layer comprises a biodegradable polymers (polycaprolactone, polyglycolic acid and/or polylactic glycolic acid); Bioactive Agents: Growth promoting (vascular endothelial growth factor, fibroblast growth factor) and antimicrobials ((antibiotics, antimicrobial peptides, naturally-occurring antimicrobial proteins); Shape: Flat sheet with non-degradable layer on one side and a degradable polymer on the other Dimensions: Overall thickness can be varied (0.1 mm-0.5 mm) as well as overall length.

Synthesis Procedure: Two polymer solutions were prepared in ice-cold 100% HFIP. The first solution prepared contained a mixture of polyurethane (PU) and polyethylene terephthalate (PET) polymers (7% and 3% w:v, respectively) with an antimicrobial agent. The second solution was composed of a mixture of polycaprolactone (PCL) and poly glycolic acid (PGA) polymers (15% and 5% w:v, respectively) with an antimicrobial agent and growth promoting factor. Both solutions were mixed for 48 hours on an inversion mixer. A self-contained computer-animated electrospinning apparatus was utilized for electrospinning. A stainless steel 58-gauge blunt spinneret (0.5 mm internal diameter) was connected to the polymer-filled syringe. The collecting surface (mandrel) was set at a jet gap distance of 15 cm from the tip of the needle. The perfusion rate was set at 3 ml per hour at 25° C. Perfusion of the polymer was then started upon application of the current to the tip of the needle (15-20 kV) with electrospinning proceeding. The PU-PET solution, which was loaded into a 10 ml syringe, was first electrospun onto a rotating 35 mm cylindrical mandrel for 90 minutes (nPU-PET). Residual HFIP on the resulting nPU-PET material was removed via sonication of the material in 100% ethanol for 30 minutes following by a sonication in water for 2 minutes. After 48 hours of drying, the PCL-PGA solution was electrospun onto the pre-existing nPU-PET polymer sheet on the mandrel, yielding the composite dermal scaffold (nPCL-PGA layer). This composite material was then vacuum-dried (600 mm Hg) at 36° C. for 24 hours to remove residual HFIP from the nPCL-PGA layer.

Bone Fixation Coating Pins

Problem: External bone fixation is a method of aligning broken bones when more conventional methods (casting, internal fixation) are precluded. In this method, pins or wires are inserted into the bone and anchored by a rigid external frame to maintain proper orientation of the fracture. This can be accomplished for temporary-stabilization pending definitive care, or can be used over a prolonged period to stabilize the fracture until union occurs. In addition, external fixation can be used for many clinical applications including limb lengthening, deformity correction, and bone transport for treating critical sized bone defects. The most common complication of external fixation is pin site infection, with reported infection rates ranging dramatically in the literature from 11-52%. Occurrence of these pin site infections is so common that they have become an accepted factor of external fixations in the healthcare industry. The entry point of a bone pin is essentially a chronic open wound, because the penetration of the pin interrupts the skin's ability to heal. These open wounds are highly susceptible to bacterial colonization and infection. External fixation pins can thus become colonized, providing a point of entry for bacteria to the soft tissues and the bone itself. This exposure of open wounds to foreign bodies provides an ideal environment for bacterial adhesion and subsequent biofilm formation, encouraging infection of adjacent tissues.

The current standard of treatment is for orthopedic surgeons to prescribe preventative pin care routines for the patient (e.g. daily bacitracin sponge washes, hydrogen peroxide washes), and to later depend on systemic and topical antibiotics when those measures fail. However, once bacteria adhere to the surface of the pin, they become highly resistant to antibiotics, allowing some infections to persist despite aggressive antibiotic treatments. The use of antibiotics that becomes necessary in these cases contributes to the development of resistant bacteria including methicillin-resistant *Staphylococcus aureus* (MRSA), and could be mitigated by a localized prophylaxis at the pin site. Pin site infections are costly, as they delay healing, prolong treatment time, and require repeat surgeries and aggressive antibiotic regimens. In many instances, the presence of persistent pin infections requires removal of the frame itself, potentially before the treatment of the underlying fracture is complete. Yet, the need for a clinically proven infection-resistant bone pin remains unanswered, and the infection rate for external bone fixations remains high. With more than $15 billion spent on orthopedic infections each year, there is a significant clinical need to impart infection-resistance to bone pins.

Composition to address Problem: Polymer Polyester (combination of polyethylene terephthalate (PET) and polybutylene terephthalate (PBT)), polyurethane or combination of polyester and polyurethane. Bioactive Agents: Antimicrobials ((antibiotics, antimicrobial peptides, naturally-occurring antimicrobial proteins); Shape: Nanofibrous coating onto metallic bone pin; Dimensions: Overall thickness can be varied (0.05 mm-0.2 mm) as well as overall length.

Synthesis Procedure: A polymer solution comprising polyethylene terephthalate (PET) with polybutylene terephthalate (PBT) (17.5% and 2% w:v, respectively) was prepared in ice-cold 100% HFIP and inversion mixed for 48 hours. This solution was then halved, and one half was kept unchanged to act as a control solution, while the other half was given 1.5% w:v of Gentamicin and mixed for another 24 hours. A self-contained, computer automated electrospinning apparatus was utilized to coat the bone pin. This apparatus can electrospin onto cylindrical constructs, such as bone pins. A stainless steel 18-gauge blunt spinneret (0.5 mm internal diameter) was connected to the polymer-filled syringe. One smooth and one surface roughened (via sandblasting) 5 mm diameter, 316L stainless steel rod (same material as a commercial bone pin) was positioned in a chuck to rotate at 270 RPMs while the spinneret was set to traverse a 4 inches length of the rod at a rate of 2 inches per second. This 4 inch length reflects the unthreaded portion of the actual bone pin (either left smooth, or sandblasted to improve adherence of the material) that would be coated. The rod was set at a jet gap distance of 15 cm from the tip of the needle. The perfusion rate was set at 3 ml/hour and +20 kV of voltage was applied to the spinneret at 25° C. Electrospinning of the polymer solution was then conducted for 10 minutes on one 4 inch section of each mandrel, and for 20 minutes on another 4 inch section of each mandrel. After the PET/PBT and PET/PBT/Gentamicin solutions were electrospun separately onto their respective 4 inch segments of cash rod, a 70° C. heat treatment at 99.99% vacuum was applied for 24 hours to seal loose fibers down to the bulk material and to remove all of the residual solvent.

Pediatric Nanofibrous Catheter Cuff

Problem: In pediatric medicine, long-term treatment of oncological, hematological, and immunological disease requires the implantation of an indwelling central venous catheter (CVC). CVCs are necessary to deliver drugs, nutritive fluids, chemotherapy, hemodialysis therapy, or to take blood samples for testing without causing trauma to the patient. Yet, CVCs are prone to failure due to three primary mechanisms: infection (3-14%), dislocation (10-19%), and thrombosis (1-2%). Infections are the primary concern with CVCs, since approximately 9-14% of pediatric patients with CVCs contract catheter-related bloodstream infections (CRBIs), the mortality rate for which is over 13%. CRBIs in pediatric patients have been reported to increase hospital stays by one week, and cost $39,219-$50,362 on average per infection, with an estimated 250.000 CRBIs occurring in the US each year 8. The other major concern is dislocation, where the CVC is accidently pulled out from the original site of implantation. This occurs most frequently in pediatric patient populations because a child's tendency to pull on the protruding catheter tubing.

Bacterial infections of CVCs originate on either the catheter's external surface or within the luminal surface. Most infections and CBRIs are caused by the migration of bacteria from the skin down the external surface of the catcher, although these infections can also migrate down to the internal lumen from the hub. Catheter infections in the lumen can be eradicated using a simple procedure called "antibiotic-, or ethanol-locks," in which either a heparinized antibiotic solution or a 70% ethanol solution is injected into the infected catheter lumen and held there for several hours. Yet, there is no comparable way to eradicate an established bacterial infection on the external surface of a catheter. Infection of the external surface requires complete removal of the CVC, possibly preventing the patient from receiving vital therapy or nutritive fluids. Thus, preventing the migration of bacteria from the skin is essential to reducing catheter infections and CRBIs.

Composition to address Problem: Polymer: Polyester (combination of polyethylene terephthalate (PET) and polybutylene terephthalate; (PBT)), polyurethane or combination of polyester and polyurethane; Bioactive Agents: Antimicrobials (antibiotics, antimicrobial peptides, naturally-occurring antimicrobial proteins); Shape: Nanofibrous coating onto a catheter device; Dimensions: Thickness can be varied (0.025 mm-2 mm); Coating length can be also varied.

Synthesis Procedure: Two polymer solutions, one containing 7% (w/v) of polyurethane 55D (PU) and 3% (w/v) polyethylene terephthalate (PET), and later another containing 7% cPU (w/v) and 3% PTT (w/v) were prepared in ice-cold hexafluoroisopropanol (HFIP). Both polymer solutions were mixed for 48 hours on an inversion mixer. Each solution was halved, with one half of each solution kept unchanged to act as a control solution, and 1.5% (w/v) of Ciprofloxacin (Cipro) was added to the other half of each solution before mixing all solutions for another 24 hours. Each solution was then placed into a 10 ml syringe for electrospinning. A self-contained, computer-automated apparatus was used to electrospin the materials. To create the materials tested in PS 1-3, a segment of polyethylene catheter tubing (14 cm length) with an inner diameter of 1.57 mm and outer diameter at 2.08 mm was used as a base material onto which the PU-PET solutions were electrospun. To create the materials, cPU-PTT solutions were electrospun directly onto a 35 mm diameter mandrel. Electrospinning parameters used for all nanofibrous catheter cuffs were: gap distance of 15 cm, applied voltage of 15 kV, perfusion rate of 3 ml/hour and electrospinning times of 5, 15, and 30 minutes (n=2 segments/electrospin time/solution). After electrospinning nanofibrous (n-)PU-PET control and Cipro-loaded cuffs, residual HFIP was removed by a sonication in ethanol for 30 minutes followed by a sonication in deionized water for 2 minutes. HFIP was removed from ncPU-PTT control and Cipro-loaded cuffs using a vacuum oven at 37° C. (99% vacuum) for 24 hours.

Other Commercial Applications

In other embodiments, nanofibrous materials with increased water moving (wicking) properties are provided. Polyester polymers are electrospun as described elsewhere in this specification. The materials are chemically treated (sodium hydroxide or ethylenediamine treated), resulting in surface functional groups. The materials can be used in various constructs for different applications that require water/solution movement.

In other embodiments, nanofibrous materials are provided to treat finger/toe nail and yeast infections (anti-fungal delivery). Polyester polymers containing antifungal agents are electrospun as described elsewhere in this specification. The resulting materials are cut and adhered to artificial finger nail or can be formed into its own device (nail coating/tampon device).

In other embodiments, nanofibrous materials with radiopaque properties are provided. Polyester, polyurethane and/or a polyurethane/polyester combination with radiopaque agents (diatrizoic acid, barium sulfate) may be synthesized as described elsewhere in this specification. The materials are useful for sutures, device location and wound dressing.

In other embodiments, nanofibrous materials are used as filtration devices. Polyester polymers are electrospun as described elsewhere in this specification. The materials are chemically treated (sodium hydroxide or ethylenediamine treated), resulting in surface functional groups. Specific bioactive moieties can be immobilized to this material and used as a filtration medium to remove targeted agents.

Series A: Preparation and Characterization of Nanofibrous (nPET) Textiles

Experiment 1. The Electrospinning Perfusion Technique

The Electrospinning Apparatus

Figure 4:
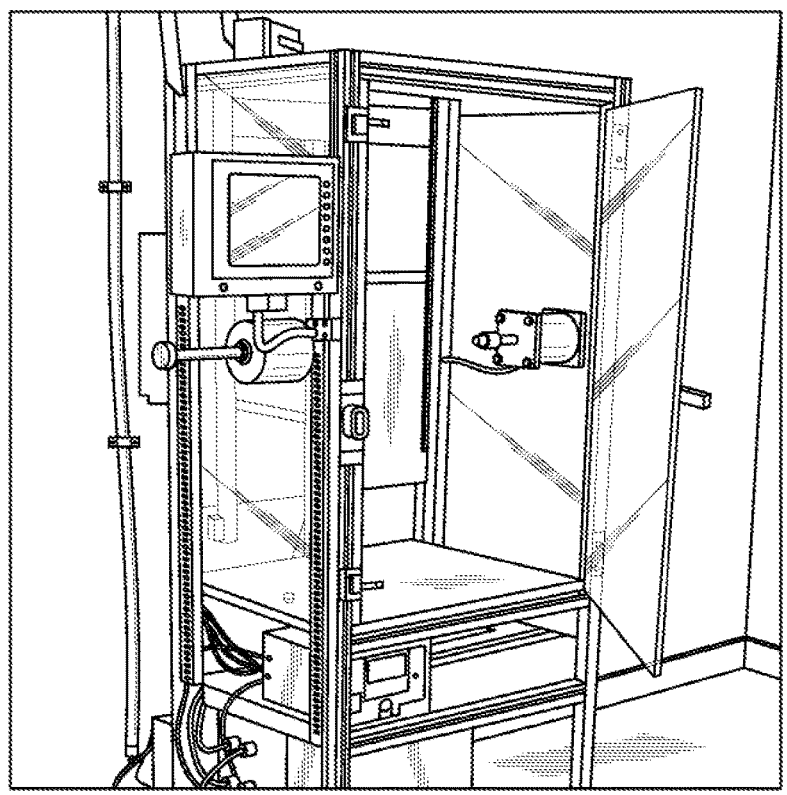
FIG. 4 is a an illustration of the apparatus for performing the electrospinning methodology.

For small batch purposes, a computer-automated electrospinning perfusion apparatus was assembled which included a power supply, a syringe pump, an elevated holding rack, a modified polyethylene chamber, a spray head with power attachment, a reciprocating system, and a stirrer for controlled mandrel rotation. Such an assembly is shown by FIG. 4.

Utilization of this assembly permits uniform coating of a liquid polymer onto the PTFE-coated stainless steel mandrel (diameter=0.75-40 mm). A 10 ml chemical-resistant syringe was filled with the liquid polymer; and a stainless steel 18 gauge blunt spinneret (0.5 mm internal diameter) was cut in half, with the syringe fitting half connected to the chemical-resistant syringe.

Nalgene PVC tubing (1/32 ID.times.3/32 OD; 66 cm length) was then connected to the syringe, followed by connection to the other half of the blunt spinneret within the spray head. The line was purged of air, with the syringe then placed onto the syringe pump. The high potential source was connected to the spray head tip; and the mandrel was set at a jet gap distance of 15 cm from the tip of the needle. The mandrel was then grounded to the power source; and the perfusion rate was set at 3 ml/hour at 25° C.

The Polymer

A polyethylene terephthalate (20% w:v) polymer was prepared in ice-cold 100% hexafluoroisopropanol. The 10 ml syringe with a stainless steel 18-gauge blunt spinneret (0.5 mm internal diameter) was filled with the solution and placed onto the Harvard Apparatus syringe pump.

The Perfusion Technique

Perfusion of the polymer was then started upon application of the current to the tip of the needle (15 kV) with electrospinning proceeding for 40 minutes. After electrospinning, the end portions of the resulting tubular structures comprised of nanofibrous polyethylene terephthalate, now termed "nPET" structures, were cut off and discarded (1 cm from each end of the mandrel). The original nPET tubular structures were then stretched 25% of the starting segment size while on the mandrel in order to provide a set stain across the fibers, a process that occurs in normal fiber extrusion. This yielded sized tubular segments of nPET fabric.

Some, but not all, of the stretched nPET segments were then immediately exposed to 100% ethanol for 2 hours at room temperature (or for 30 minutes in 100% ethanol with sonication) in order to remove the residual solvent. Then, all of the nPET tubular structures (ethanol exposed or not) were air-dried overnight at room temperature.

Results

The nPET tubular segments, whether air-dried or exposed to ethanol followed by air-drying, had a consistent 4 mm internal diameter throughout the lumen (length=7.5 cm). A total of 4 nPET structures were synthesized for each method using the above-described process.

For this experimental study, the nPET segments air-dried at 60° C. were employed for all of the subsequently conducted in-vitro studies reported herein. This post-synthesis treatment was performed owing to the possibility of Cipro eluting during the ethanol incubation for the other methodology described later herein.

Concerning the electrospinning technique itself for tubular structures fabricated using the described parameters, it was found that increasing electrospinning time significantly beyond 40 minutes increased the rigidity of the resulting nPET material. Conversely, electrospinning the liquid polymer blending for shorter periods of time (e.g., 1-15 minutes) provided a tubular structure without significant (less than 1 pound break strength) wall strength. Major differences in and variance of tubular wall rigidity may be desired for the various medical articles and devices to be employed clinically. However, the chosen parameters employed for nPET material formation in these experimental studies were uniformly and consistently maintained at 40 minutes of electrospinning time, a polymer concentration of 20%, an applied voltage (15 kV), and a gap distance of 15 cm.

Experiment 2: Characterization of Physical Properties of Electrospun nPET Material Tensile Strength/Ultimate Elongation Tensile strength (pounds force), strain at maximum load (%) and strain at break (%) for knitted DACRON segments (formed of a commercially obtained standard textile material) and for electrospun nPBT segments (formed of a polyethylene terephthalate compound prepared as described above) were measured using previously published techniques. Control and test segments (7 mm width, 3 cm length; n=3/test condition) of both kinds of material were measured and cut.

A Q-Test Tensile Strength Apparatus (MTS Systems, Cary, N.C.) was calibrated according to manufacturer's specifications in a climate-controlled environment (room temperature=70° F., 65% relative humidity). Each of the samples under test were also conditioned in this environment for 24 hours. Segment stretching (crosshead speed=50 mm/min. gauge length=2 cm, load cell=25 lb) was then initiated and terminated upon segment breakage.

Results

There was a marked difference between the break load of knitted DACRON segments (42±9 pounds force) and electrospun nPET segments (3.7±0.9 pounds force). This difference in breaking load was expected owing to the significantly greater wall thickness of the knitted DACRON material. The other physical properties, such as the percent strain al maximum load (60±24 versus 55±8) and percent strain at break (60 versus 62±3), were comparable between the two test materials, indicating that the difference in break strength was directly related to wall thickness. Thus, the nPET material is shown to possess significant physical characteristics that would permit its presence and application in various medical devices.

Experiment 3: Evaluation of Electrospun nPET Material Via Scanning Electron Microscopy Scanning Electron Microscopy (SEM)

Two electrospun nPET segments were randomly selected and examined via a JBOL JSM 5900 LV electron microscope in order to determine fiber size and distribution throughout the material wall.

Results

Analysis of electrospun nPET tubular structures via SEM revealed that the diameter of the polyethylene terephthalate fibers comprising the nanofibrous material varied from about 100 nm to 3000 nm in size. This is shown by the microphotographs of FIG. 5A and FIG. 5B. A comparison SEM analysis of the knitted DACRON samples revealed that the knitted DACRON fibers ranged from 15 to 30 micrometers in diameter size (data not shown) and thus were significantly larger than the nPET fiber diameter size range.

Series B: The Agent-Releasing Textiles Comprising the Present Invention

Experiment 4: Synthesis of Novel nPET Materials with Biologically Active Agents

Prior to forming the blended polymer solution, the solubility of Cipro, Diflucan and Paclitaxel in the HFIP (hexafluoroisopropanol) solvent was determined. Based on the prechosen concentration of active agent to be employed in the composite, 15 mg of each respective agent was placed into 1 ml of the HFIP solvent, mixed and observed.

Following this initial assessment, polyethylene terephthalate (19%) polymer solutions containing either Cipro, or Diflucan, or Paclitaxel (1.5% w:v) respectively were prepared in ice-cold 100% hexafluoroisopropanol. These individually prepared polymer solutions of Cipro, or Diflucan, or Paclitaxel were mixed on an inversion mixer for 48 hours in order to completely solubilize both the polyethylene terephthalate polymer and each active agent component in their respective individual solutions. Then, the self-contained, semi-automated electrospinning apparatus (described previously herein) was again employed for fabricating each version of nanofibrous textile material.

Utilization of this system permits uniform coating of the prepared polyethylene terephthalate polymer solution onto the PTFE-coated stainless steel mandrel (diameter=4 mm). Using the uniform set of parameters of the previously described experimental series, the mandrel was set at a jet gap distance of 15 cm from the tip of the needle. The mandrel was then grounded to the power source. The perfusion rate was set at 3 ml/hour at 25° C. Perfusion of the polyethylene terephthalate/active agent mixture was then started upon application of the current to the tip of the needle (15 kV) with electrospinning proceeding for 40 minutes. After electrospinning, the end portions of the original tubular structure (1 cm from each end of the mandrel) were cut off and discarded. This resulted in textile tubular segments of fixed length.

The resulting tubular segments were then stretched 25% of the starting segment size while on the mandrel in order to provide a set strain across the fibers, a process that occurs in normal fiber extrusion. These tubular segments were then either air-dried at 60° C. overnight; or exposed to 100% ethanol for 2 hours at room temperature in order to remove the residual solvent. Due the fluorescent properties of Cipro, nPET segments (those having no active agent) and nPET-Cipro segments (those having Cipro as the active agent)—having been already exposed to 60° C. temperature overnight or to 100% ethanol for 2 hours—were then exposed to a hand-held UV light to qualitatively assess Cipro presence within the textile structure.

Results

Cipro, Diflucan and Paclitaxel individually were each found to have excellent solubility in the HFIP solvent. Once combined with the polyethylene terephthalate polymer/HFIP liquid, the solubility of each respective active agent remained unchanged. Formation of nPET (as a substantive material) and of nPET tubular structures containing either Cipro, or Diflucan, or Paclitaxel were all successfully accomplished. All these structures showed a consistent 4 mm internal diameter throughout the lumen for each tubular structure (material length=7.5 cm). Based on the perfusion rate in conjunction with electrospinning time, each tubular segment incorporated approximately 30 mg of each respective active agent.

In addition, similarly to our previous experimental series, increasing electrospinning time significantly increased the rigidity of the resulting nanofibrous material. Conversely, electrospinning for shorter periods of time (1-15 minutes) provided a tubular structure without significant wall strength.

Furthermore, gross observation of the various resulting tubular segments via UV illumination revealed intense fluorescence from the nPET-Cipro segments, whether air-dried or ethanol washed, when compared to the nPET segments. This UV illumination data demonstrated the presence of Cipro to be only within the nPET-Cipro segments. This effect is illustrated by FIG. 6.

Experiment 5: Determination of Cipro and Diflucan Release from nPET-Cipro and nPET-Diflucan Segments Via UV/VIS Spectrophotometer Methods nPET segments, nPET-Cipro segments, and nPET-Diflucan segments (0.5 cm segment length, n=3 segments/time interval/segment treatment) were individually placed into 5 ml of phosphate buffered saline (PBS) followed by continuous agitation using Rugged Rotator inversion mixer (33 r.p.m.) at 37° C. Wash solutions were sampled at acute (0, 1, 4 and 24 hours) and chronic (2-21 days for Cipro and 2-7 days for Diflucan) time periods, with replacement of the wash solution with a fresh 5 ml PBS after sampling. The absorbance of wash solutions were read at 322 nm (PBS blank) using a Beckman DU640 UV/VIS spectrophotometer.

A standard curve using known Cipro concentrations ranging from 0-100 micrograms per ml was prepared. This Cipro standard curve was then used to extrapolate the antibiotic concentration within the wash solutions.

Results

Figure 7:
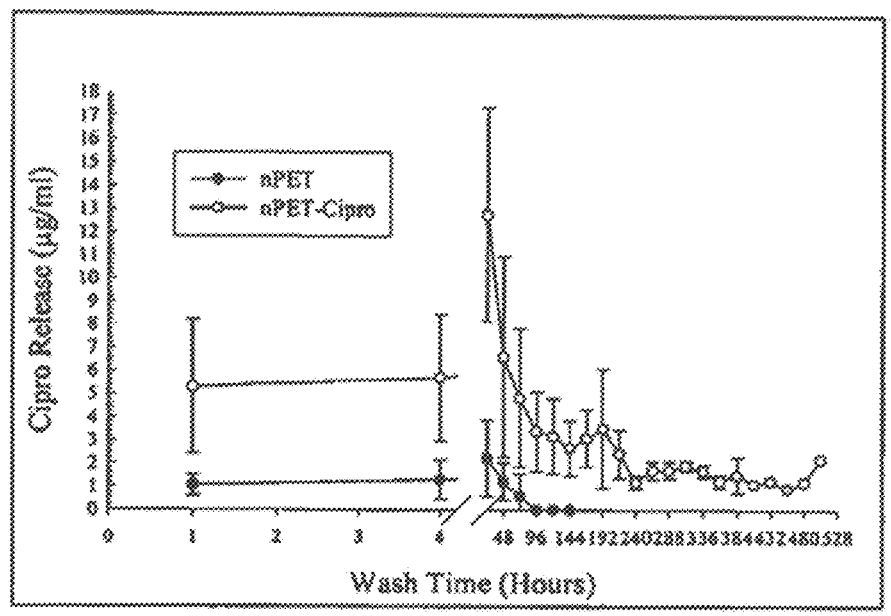
FIG. 7 is a graph showing the release profile of Cipro from nPET-Cipro segments over time.
Figure 8:
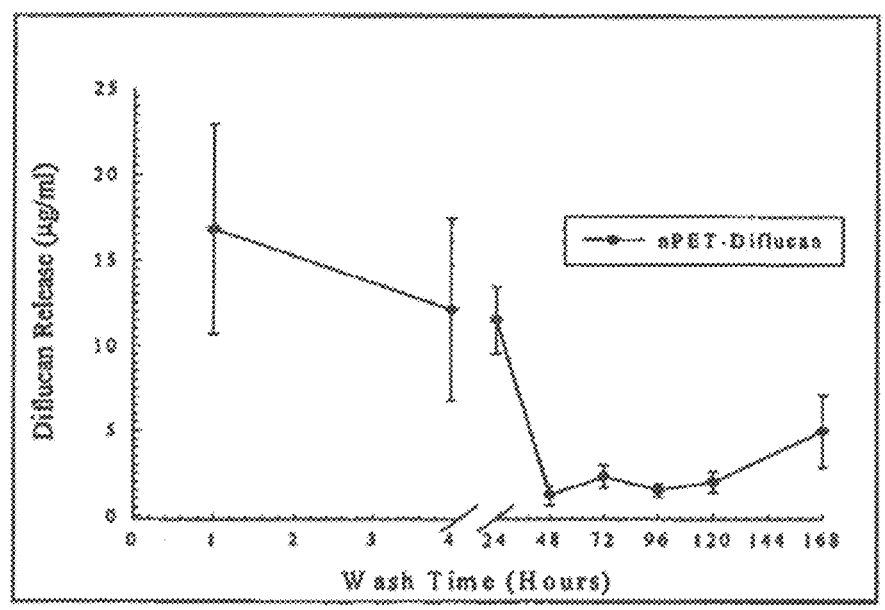
FIG. 8 is a graph showing the release profile of Diflucan from nPET-Diflucan segments over time.

The release profiles for the nPET-Cipro segments are shown by FIG. 7, and the release profiles for the nPET- Diflucan segments are shown by FIG. 8. Notably, the release profiles for each type of segment are markedly different.

As observed and recorded, Cipro release within the first 4 hours was consistent at 5±2 micrograms per ml, and was followed by a sharp increase in rate to 13±4 micrograms per ml at 24 hours. Cipro release then decreased to 6±4 micrograms per ml by 48 hours, but persisted (ranging from 1-2 micrograms per ml) throughout the time duration of this study (504 hours). The amount of Cipro released has significant biological activity, owing to the low $MIC_{50}$ for Cipro (0.26 micrograms per ml).

In comparison, Diflucan release followed typical first order kinetics in that the greatest release occurred within the first 24 hours (17, 12 and 11 micrograms per ml, respectively). This was followed by a slow sustained release over the remaining time periods over the 168 hour study period, the time duration of this study.

Overall therefore, nPET segments containing Cipro and Diflucan demonstrated significant release of each active agent throughout the time periods empirically evaluated.

Experiment 6: Antimicrobial Activity of nPET Segments and nPET-Cipro Segments Via a Zone of Inhibition Assay Methods nPET segments (n=3 segments/time interval) and nPET-Cipro segments (n=9 segments/time interval), which were previously washed as described above, were then evaluated for antimicrobial activity using a zone of inhibition assay.

Figure 9:
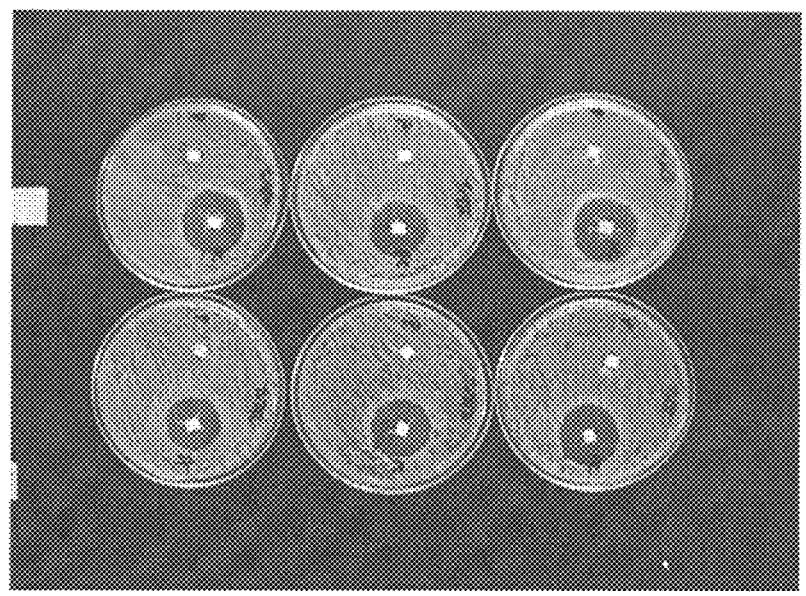
FIG. 9 is an overhead view of the inhibitions zone against *Staphylococcus aureus* streaked onto agar plates.

A stock solution of *S. aureus* was thawed at 37° C. for 1 hour. Upon thawing, 1 microliter of this stock was added to 5 ml of Trypticase Soy Broth (TSB) and incubated overnight at 37° C. From this solution, 10 microliters was streaked onto Trypticase Soy Agar (TSA) plates. nPET segments and nPET-Cipro segments were individually embedded into the *S. aureus* streaked TSA plates; and each prepared plate was then placed into a 37° C. incubator overnight. Standard 5 micrograms Cipro Sensi-Discs (n=3) were also embedded into the *S. aureus* streaked TSA plates at each time interval as a positive control. The zone of inhibition each piece was determined, taking the average of 3 individual diameter measurements. Zone size (mm) over time was determined for each parameter. The prepared assay plates are illustrated by FIG. 9.

Results

Figure 10:
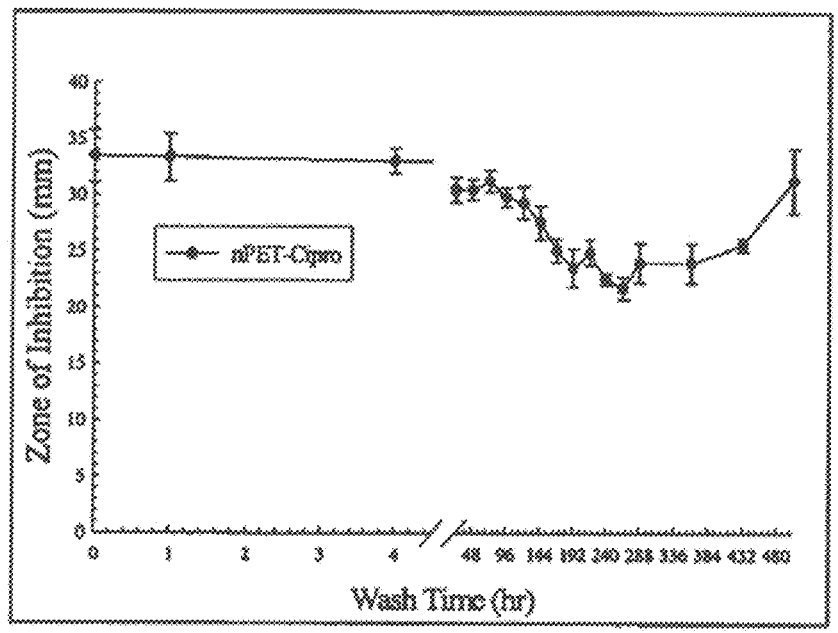
FIG. 10 is a graph showing the antimicrobial activity of nPET-Cipro segments over time.

The nPET-Cipro segments demonstrated significantly greater antimicrobial activity than nPET segment controls at all of time periods examined. This is graphically shown by the data of FIG. 10.

The zone of inhibition created by the 5 micrograms Cipro Sensi-Discs was consistent at 23 mm. The nPET-Cipro segment antimicrobial activity profile correlated with the Cipro release determined in the spectrophotometric studies—in that the greatest antimicrobial activity occurred within the first 48 hours. Cipro antimicrobial activity, presumably caused by lower Cipro concentrations being released over time as determined by the spectrophotometry, decreased slowly over the remaining time periods. Nevertheless, significant antimicrobial activity was still evident even after 504 tours, with inhibition zones being comparable to those of the Sensi-Disc results. Thus, this study demonstrates that Cipro release from the nPET material persisted for over 504 hours, with antimicrobial activity correlating to the quantity of Cipro release.

Experiment 7: Anti-Fungal Activity of nPET Segments and nPET-Diflucan Segments Using a Turbidity Assay Methods

*Candida albicans* was purchased from ATCC. The fungus was re-hydrated in YM Broth with 0.5% dextrose and grown for 30 hours at 30° C. under humidified conditions. nPBT segments and nPET-Diflucan segments (1 square cm, n=2 segments/inoculum/treatment) were prepared as previously described herein, and then tested against various *Candida albicans* concentrations.

A broth macrodilution assay was performed based on the NCCLS M27-A protocol. The stock fungal inoculum concentration was determined via backplating a set volume of the diluted fungus broth onto Trypticase Soy Agar plates. The number of colony forming units (cfu) grown per plate was then counted and extrapolated to determine the starting *Candida* concentration.

The stock fungus solution was then diluted to $10^6$, $10^5$ and $10^4$ cfu/ml. After incubating the individual test segments in 2 ml of the fungus solutions for 24 hours at 30° C., the optical density of the broth solutions was measured at 492 nm. These values were compared to *Candida* solutions without any nPET materials (serving as the positive control) as well as against YM Broth only and *Candida* solutions with 40 micrograms Diflucan solution (both serving as negative controls).

Results

Figure 11:
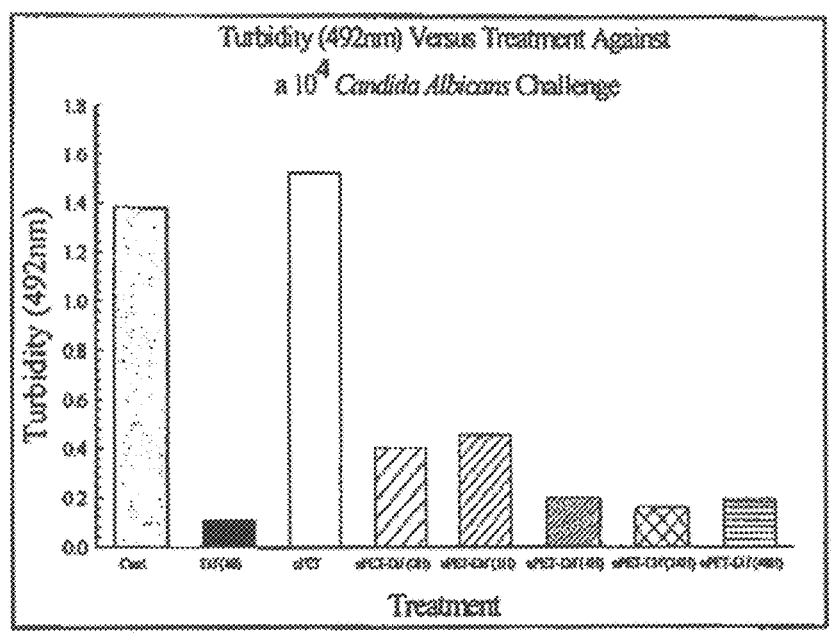
FIG. 11 is a graph showing the anti-fungal activity of nPET-Diflucan segments against varying concentrations of *Candida albicans*.

The nPBT-Diflucan segments had significantly greater antifungal activity at all wash periods as compared to nPET segments which had no antifungal activity (turbidity comparable to *Candida* control). This is graphically shown by the data of FIG. 11.

Diflucan (40 micrograms) in solution demonstrated excellent antifungal activity against this inoculum, with decreasing activity as the inoculum increased. Antifungal activity by the nPET-Diflucan segments was clearly evident at all *Candida* concentrations evaluated with activity mimicking solution-based Diflucan (data not shown). Thus, this experimental study demonstrated that Diflucan is released from the electrospun nanofibrous material even after extensive washing for 2 days, with Diflucan maintaining it recognized and characteristic antifungal activity after synthesis of the nPET-Diflucan tubular structure.

Experiment 8: Development of Electrospinning Methodology for Flat Sheet Nanofibrous (nPET) Material Methods As described in Series A above, prepared polyethylene terephthalate chips were dissolved in ice-cold 100% hexafluoroisopropanol (19% w:v) and mixed on an inversion mixer for 48 hours in order completely solubilize the chips. The self-contained, semi-automated electrospinning apparatus containing a Glassman power supply, a Harvard Apparatus syringe pump, an elevated holding rack, a modified polyethylene chamber, a spray head with power attachment and a reciprocating system was again used.

The stirrer was used to provide a holding chamber for the new flat collecting plate employed to generate a sheet format. The design of this surface is based upon the collecting plate. In short, a flat 12 cm.times.10 cm copper plate, containing a 6 cm stainless steel rod extending from the underside of the plate was designed and grounded to the power source.

A 10 ml chemical-resistant syringe was filled with the polymer liquid. A stainless steel 18-gauge blunt spinneret (0.5 mm internal diameter) was then cut in half, with the syringe fitting end connected to the polymer-filled syringe. Nalgene PVC tubing was connected to the syringe filled with the polymer solution followed by connection to the other half of the blunt spinneret within the spray head. The line was then purged of air, with the syringe then placed onto the syringe pump. The high potential source was connected to the spray head tip, with the plate set at a jet gap distance of 15 cm from the tip of the needle. The perfusion rate was set at 3 ml/hour at 25° C.

Figure 12:
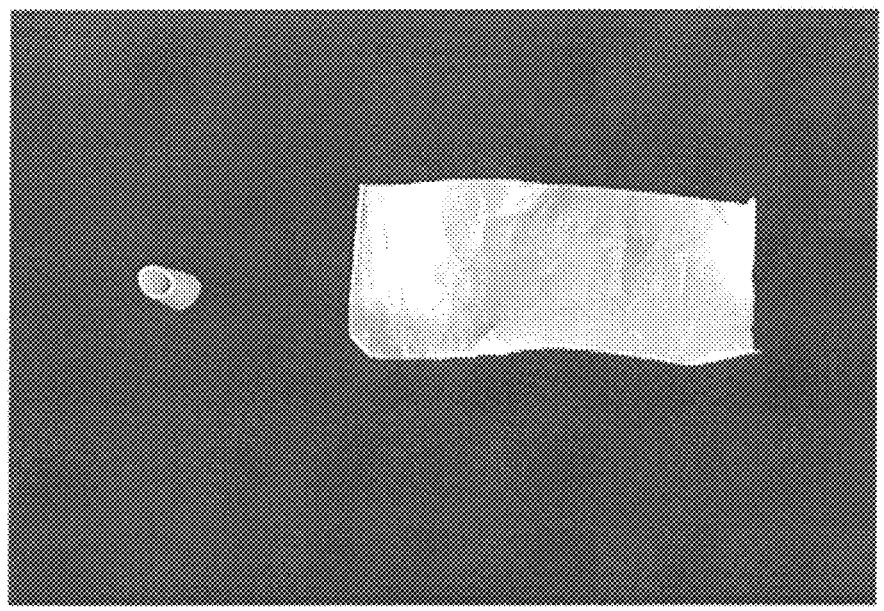
FIG. 12 illustrates an overhead view of a flat sheet of electrospun textile fabric.

Perfusion of the polymer liquid was started upon application of the current to the tip of the needle (15 kV) with electrospinning proceeding for 1 hour and 40 minutes, with rotation of the plate 20° every 20 minutes. This resulted in a flat, planar sheet of nPBT nanofibrous material being formed. The resulting nPET sheet is illustrated by FIG. 12.

After the electrospinning procedure was completed, a 1.0 cm margin around the perimeter edge of the entire nPET planar sheet was cut off in order to eliminate potential variability in the fabric thickness along the edge. The flat nPET sheet construct was then stretched 25% in the width and length of the material in order to provide a uniform set strain across the fibers, followed by air-drying at 60 overnight.

Results

A flat sheet of electrospun nPET textile fabric (8 cm.times.10 cm) was formed using this alternative method and technology. When viewed in gross, the nPET planar sheet had excellent handling characteristics and possessed physical properties comparable to the nPET tubular structures.

VII. Conclusions Drawn from and Supported by the Empirical Data

1. The self-contained, semi-automated electrospinning apparatus provided by the present invention can be employed to generate two different formats of nanofibrous textile fabrics. One format is a tubular structure having determinable inner wall and outer wall diameter sizes, two open ends, and an internal lumen typically less than about 6 millimeters in diameter. This tubular structure format presents an interior wall surface and an exterior wall surface, and is a conduit biocompatible with and suitable for the conveyance of liquids and gases through its internal lumen.

A second format is a Hat or planar sheet construction having determinable, length, width, and depth dimensions. The flat sheet fabric can be folded and refolded repeatedly; can be cut and sized to meet specific configurations; is resilient and can be prepared in advance to provide varying degrees of flexibility, springiness, suppleness, and elasticity.

2. A wide range and variety of agent-releasing textiles can be prepared for use as medical articles and devices using the present invention. The agents are biologically active and well characterized; are incorporated in chosen concentrations as an ingredient in the bulk polymer prior to making the textile fabric; and become indefinitely attached to and non-permanently immobilized upon the fabricated nanofibrous textile material as a concomitant part of the process for manufacturing the textile.

3. After being placed in a water containing environment, the agent-releasing textile will begin to take up water, release its incorporated biologically active agent in-situ over time; and deliver the release active agent at measurable concentrations directly into the adjacent and surrounding milieu. The in-situ released agent is function, operative and potent; and provides/performs its well recognized and characteristic biologically activity whenever and wherever it is delivered.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A method of forming a fabricated textile comprising nanofibers by electrospinning perfusion, the method comprising the steps of:
   dissolving 19-20% weight per volume of a non-biodegradable polymer in hexafluoroisopropanol to provide an admixture, the dissolving occurring at an ice-cold temperature, wherein the non-biodegradable polymer is not polytetrafluoroethylene, polypropylene, or polyethylene;
   loading the admixture into an electrospinning perfusion instrument which can be set at a specified flow rate;
   applying an electric current of 15-20 kV to a needle of the electrospinning perfusion instrument;
   perfusing the admixture onto a target surface at the specified flow rate, the step of perfusing occurring at a temperature between about 20° C. and about 50° C. to provide a perfused nanofiber having a diameter from 100 nm to 3000 nm; and
   permitting trace hexafluoroisopropanol to be removed from the perfused nanofiber to form a fabricated textile.

2. The method of claim 1, further comprising dissolving at least one biologically-active agent such that the admixture comprises a mixture of the non-biodegradable polymer and the at least one biologically active agent.

3. The method of claim 1, wherein the step of permitting trace hexafluoroisopropanol to be removed is performed using a post-treatment process performed after the step of perfusing the admixture.

4. The method of claim 1, wherein the target surface is a mandrel.

5. The method of claim 1, wherein the target surface is a metallic stent that is slid onto a mandrel and coated with perfused material, and wherein the coated metallic stent is air-dried in a vacuum oven at 37° C. for 48 hours to remove residual hexafluoroisopropanol.

6. The method of claim 1, wherein the non-biodegradable polymer is selected from the group consisting of a non-biodegradable polyester, a polyurethane, and combinations thereof.

7. The method of claim 1, wherein the target surface comprises a first portion and a second portion and the step of perfusing the admixture onto the target surface perfuses the admixture for a first period of time onto the first portion and for a second period of time onto the second portion, wherein the first period and the second period are different.

8. The method of claim 1, the method further comprising removing the perfused fabricated textile from the target surface.

9. The method of claim 4, wherein the perfused fabricated textile is formed into a tubular construct.

10. The method of claim 9, wherein the tubular construct has an internal diameter of at least 1 mm and less than 40 mm.

11. The method of claim 9, wherein the tubular construct has a length of at least about 1 cm and less than about 80 cm.

12. The method of claim 4, wherein the perfused fabricated textile coated mandrel is processed to remove traces of residual solvent and one edge of the perfused material is rolled towards an opposite end of the mandrel to achieve a desired thickness, and wherein the perfused material is cut along an opposite edge and the opposite edge is fused to form a rounded cuff shape.

13. The method of claim 8, wherein the perfused fabricated textile is a flat sheet with a width of at least 1 cm and a length of at least 1 cm.

14. The method of claim 13, further comprising fusing the perfused fabricated textile to a second flat sheet comprising a biodegradable polymer.

15. The method of claim 1, wherein the step of dissolving further comprises dissolving a biodegradable polymer such that the admixture comprises a mixture of the non-biodegradable polymer and the biodegradable polymer.

16. The method of claim 2, wherein the at least one biologically-active agent is maintained at a temperature below about 50° C. during the steps of dissolving, loading, perfusing and permitting such that the at least one biologically active agent maintains the same biological activity after the method as the at least one biologically active agent had before the method.

17. The method of claim 1, wherein the target surface is configured to create alignment of polymer nanofibers in a toroidal direction with respect to a revolution of the target surface.

18. The method of claim 17, wherein the polymer nanofibers are removed from the target surface and manually twisted and elongated to their yield strain to produce a single-strand yarn shape.

19. The method of claim 18, wherein the single-strand yarn shape has a diameter between about 0.025 mm and about 2 mm.

20. The method of claim 1, wherein a 15-30 centimeter jet gap exists between the needle and the target surface.

21. The method of claim 1, wherein a 15 centimeter jet gap exists between the needle and the target surface.

22. The method of claim 1, wherein the fabricated textile is formed into a medical device without the use of an underlying scaffold.

* * * * *

UNITED STATES PATENT AND TRADEMARK OFFICE
CERTIFICATE OF CORRECTION

PATENT NO.       : 10,441,550 B2
APPLICATION NO.  : 15/046675
DATED            : October 15, 2019
INVENTOR(S)      : Matthew D. Phaneuf et al.

Page 1 of 1

It is certified that error appears in the above-identified patent and that said Letters Patent is hereby corrected as shown below:

In the Claims

Correction of Claim 1 is requested as follows:
Column 38
Line 44, please change "provide a perfused nanofiber having a diameter from" to --provide perfused nanofiber having a diameter from--

Correction of Claim 12 is requested as follows:
Column 39
Line 19, please change "residual solvent and one edge of the perfused material is" to --residual hexafluoroisopropanol and one edge of the perfused material is--

Signed and Sealed this
Twenty-first Day of January, 2020

Andrei Iancu
*Director of the United States Patent and Trademark Office*